United States Patent
Guenat et al.

(10) Patent No.: US 12,359,153 B2
(45) Date of Patent: Jul. 15, 2025

(54) CELL CULTURING SYSTEM AND METHOD

(71) Applicants: AlveoliX Technologies AG, Bern (CH); UNIVERSITÄT BERN, Bern (CH)

(72) Inventors: Olivier Thierry Guenat, Bern (CH); Janick Daniel Stucki, Bern (CH); Marcel Aeschlimann, Ligerz (CH); Christophe Léchot, Biel (CH)

(73) Assignees: AlveoliX Technologies AG, Bern (CH); UNIVERSITÄT BERN, Bern (CH)

(*) Notice: Subject to any disclaimer, the term of this patent is extended or adjusted under 35 U.S.C. 154(b) by 0 days.

(21) Appl. No.: 18/304,957

(22) Filed: Apr. 21, 2023

(65) Prior Publication Data
US 2023/0250375 A1   Aug. 10, 2023

Related U.S. Application Data

(63) Continuation of application No. 16/462,166, filed as application No. PCT/EP2017/080259 on Nov. 23, 2017, now Pat. No. 11,655,439.

(30) Foreign Application Priority Data

Nov. 24, 2016   (EP) .................................. 16200451

(51) Int. Cl.
*C12M 3/00*   (2006.01)
*C12M 1/00*   (2006.01)
(Continued)

(52) U.S. Cl.
CPC ............ *C12M 21/08* (2013.01); *C12M 23/12* (2013.01); *C12M 23/42* (2013.01); *C12M 23/44* (2013.01);
(Continued)

(58) Field of Classification Search
CPC ...... C12M 21/08; C12M 23/12; C12M 23/42; C12M 23/44; C12M 23/58; C12M 25/02; C12M 29/10; C12M 35/04; C12M 33/04
See application file for complete search history.

(56) References Cited

U.S. PATENT DOCUMENTS

2007/0155007 A1* 7/2007 Kan ...................... C12M 23/20
                                                                435/297.5
2008/0280290 A1* 11/2008 Dawson ................ B01L 3/5085
                                                                435/6.12
(Continued)

FOREIGN PATENT DOCUMENTS

DE   100 46 175 A1   3/2002
JP   2007-537732 A   12/2007
(Continued)

OTHER PUBLICATIONS

Machine Translation of JP-2009521228-A (Year: 2024).*
(Continued)

*Primary Examiner* — Michael L Hobbs
(74) *Attorney, Agent, or Firm* — MEDLER FERRO WOODHOUSE & MILLS PLLC

(57) ABSTRACT

A culturing membrane comprising a support provided by a mesh with holes filled with extracellular matrix proteins, as well as a method of producing a culturing membrane made of components found in a basal membrane, comprising the steps of using a mesh having holes; and providing a solution with the components found in the basal membrane on the mesh.

15 Claims, 10 Drawing Sheets

(51) Int. Cl.
  *C12M 1/12* (2006.01)
  *C12M 1/32* (2006.01)
  *C12M 1/42* (2006.01)

(52) U.S. Cl.
  CPC ............ *C12M 23/58* (2013.01); *C12M 25/02* (2013.01); *C12M 29/10* (2013.01); *C12M 35/04* (2013.01)

(56) References Cited

U.S. PATENT DOCUMENTS

| | | | |
|---|---|---|---|
| 2011/0250585 A1* | 10/2011 | Ingber | B01L 3/50273 977/773 |
| 2014/0212964 A1 | 7/2014 | Cuiffi et al. | |
| 2018/0230415 A1* | 8/2018 | Huh | A61L 27/52 |

FOREIGN PATENT DOCUMENTS

| | | | | |
|---|---|---|---|---|
| JP | 2008079598 A | | 4/2008 | |
| JP | 2009521228 A | * | 6/2009 | ........... C12N 5/0639 |
| WO | 2005-104755 A2 | | 11/2005 | |
| WO | 2006/033935 A2 | | 3/2006 | |
| WO | 2013/082612 A1 | | 6/2013 | |
| WO | 2013/086486 A1 | | 6/2013 | |
| WO | 2014/018770 A1 | | 1/2014 | |
| WO | 2014/048637 A1 | | 4/2014 | |
| WO | 2015/032889 A1 | | 3/2015 | |
| WO | 2016/022722 A1 | | 2/2016 | |
| WO | WO-2016112245 A1 | * | 7/2016 | ............. A61K 35/17 |

OTHER PUBLICATIONS

Office Action issued on Jul. 4, 2023 in JP Appl. No. 2022-092890.
International Search Report and Written Opinion issued Mar. 1, 2018 in corresponding International Patent Application No. PCT/EP2017/080259.
Domansky et al., "Perfused multiwell plate for 3D liver tissue engineering," The Royal Society of Chemistry, Lab Chip, vol. 10, pp. 51-58, 2010.

* cited by examiner

CELL CULTURING SYSTEM AND METHOD

CROSS-REFERENCE TO RELATED APPLICATIONS

The present application is a continuation of prior application U.S. application Ser. No. 16/462,166, having a 371(c) date of May 17, 2019, which is a national phase application of PCT/EP2017/080259, filed Nov. 23, 2017, which claims priority to EP 16200451.9, filed Nov. 24, 2016, each of which is incorporated by reference herein in its entirety.

TECHNICAL FIELD

The present invention relates to a cell culturing system for culturing cells on a culturing membrane. Such systems can be used to mechanically stimulate, perfuse and/or interconnect in-vivo-like tissues. It can either be used as array of tissues mimicking a single organ or as multi-organs system connecting different tissues with each other or a combination thereof.

BACKGROUND

Advanced in-vitro models of human tissues that reproduce the dynamic environment found in-vivo and/or the interplay between different tissues are often complex systems that make their construction and handling complicated and incompatible with automatic pipetting robots widely used in the pharmaceutical industry. Several approaches aimed at providing perfused cell culture systems have been proposed over the past decade most of them rely on integrated peristaltic pumps or on systems that are based on pressurized cell culture media reservoirs.

For example, WO 2014/018770 A1 describes a modular device for culturing cells, comprising an array of cell culture vessels reversibly coupled to a control plate that integrates actuators to transport a fluid flow between the cell culture vessels.

Further, in WO 2014/048637 A1 a similar approach is used for a multi-organ-chip device that comprised a self-contained circulation system, driven by a peristaltic micropump integrated in the microfluidic chip.

Still further, WO 2013/082612 A1 describes a system which avoids the integration of an array of pumps by using a pressurized system to perfuse cell cultures in parallel. A multi-well plate with an array of bioreactors is equipped with a coverlid tightly adjusted to pressurize reservoirs located underneath. A major drawback of the system is the inability to access the cells during perfusion due to the presence of the coverlid tightly attached to the well plate. In addition, the system is not simple to handle due to the coverlid that is connected with several fluidic tubings.

However, even though the mentioned systems are modular and can be used in automatic or semi-automatic processes they do not allow to mimic real situations in which the cells or the substrates carrying the cells are stressed such as by mechanical forces like compression and tension.

Therefore, there is a need for a system and a method allowing a modular automatic cell culturing application and being capable of mimicking the situations of the cultured cells as close to in-vivo situations as possible.

BRIEF SUMMARY

According to the invention this need is settled by a cell culturing system as described herein. Preferred embodiments are subject of the dependent claims.

In particular, a cell culturing system is suggested which comprises a docking station, a handling unit, a culturing module and an actuation layer. Preferably, the system is provided with at least two structurally identical culturing modules. The culturing module has a culturing well. The handling unit has a seat for accommodating the culturing module and the actuation layer and a bottom with an actuation bore associated to the culturing well and the bottom is separated from the culturing module by the actuation layer. The docking station has a coupling structure for removably holding the handling unit in a predefined position and an actuation feeding channel, wherein, when the handling unit is held by the coupling structure in the predefined position, a first end of the actuation feeding channel is connected to the actuation bore and a second end of the actuation feeding channel is connected to a connector.

Preferably, the handling unit is dimensioned according to microplates standards. Such standards can particularly be established standards for microtiter plates such as a standard microtiter plates having 96 wells, 384 wells or 1536 wells. Widespread such standards are developed by the Society for Biomolecular Screening (SBS) and approved by the American National Standards Institute (ANSI). These standards define microtiter plates of 127.76 mm length, 85.48 mm width and 14.35 mm height comprising 96, 384 or 1536 wells (see Society for Biomolecular Screening. ANSI/SBS 1-2004: Microplates—Footprint Dimensions, ANSI/SBS 2-2004: Microplates—Height Dimensions, ANSI/SBS 3-2004: Microplates—Bottom Outside Flange Dimensions and ANSI/SBS 4-2004: Microplates—Well Positions. http://www.sbsonline.org: Society for Biomolecular Screening, 2004.). Using such a standardized module allows for applying the system with commonly used tools such as pipetting robots and the like. In particular it can be compatible with standard equipment such as multipipettors and automatic pipetting robots commonly used in cell biology laboratories.

The culturing module can be integral with the handling unit or fixedly accommodated to the seat of the handling unit. However, preferably the seat of the handling unit is arranged for removably accommodating the culturing module and the actuation layer and the actuation bore is associated to the culturing well and the bottom is separated from the culturing module by the actuation layer when the culturing module is arranged in the seat.

The term "removably" in connection with the seat of the handling unit and the coupling structure of the docking station relates to a holding or coupling which is releasable. Thereby, the handling unit can be coupled to the docking station and released from it as desired. Similarly, the culturing module can be held in the seat of the handling unit and released from it as desired.

In one embodiment the actuation layer can be used for culturing or growing cells. This can allow for reducing the number of components in the system and to provide a comparably simple construction. However, the culturing module preferably has a culturing membrane separating the culturing well in an apical culturing chamber and a basal culturing chamber.

When applying the cell culturing system cells can be seeded and grown on one or both sides of the culturing membrane or the actuation layer in the culturing well of the culturing module. Like this, cells can be grown in the apical as well as the basolateral or basal chamber of the culturing well. For mimicking conditions as they occur in-vivo a pressure, e.g., in the basolateral chamber can be changed by providing an over- or under-pressure to the connector of the actuation feeding channel of the docking station. Via the actuation feeding channel and the actuation bore the pressure change induces a positive or negative deflection, e.g. pushed away from the actuation bore or pulled into the actuation bore, of the actuation membrane which separates the actuation bore from the culturing well of the culturing module. Like this, the pressure inside the culturing well such as in the basolateral chamber thereof correspondingly changes which induces a respective positive or negative deflection of the culturing membrane. Like this, real life or in vivo conditions can be mimicked which makes the conditions the cells are exposed to more realistic. For example, the membrane can be moved or stressed as it occurs in the lungs. Additionally or alternatively, the mentioned pressure can induce a change in a flow of a medium inside the culturing well. Thus, the pressure applied to the actuation layer may be used to control the flow of the medium.

In a particularly efficient embodiment, the culturing module has a plurality of culturing wells. For example, it can have one or more lines or series of culturing wells. Also it can be equipped with plural inlet and outlet wells as described in more detail below. Thereby, the plural inlet and outlet wells can extend parallel to the one or more lines of series of culturing wells. In particular, the one or more lines of series of culturing wells can be arranged in between the inlet and outlet wells.

The cell culturing system can be designed as an array of similar tissues that can be exposed to various mechanical stresses, such as cyclic stress of the respiration, shear stress induced by perfusion or other mechanical forces such as compression or tension or a combination thereof. The location of the pressurizable bores at the bottom of the handling unit allows the cell culturing module and handling unit to be completely free of tubings. It can, thus, easily be designed to be compatible to automatic pipetting robots or standard microscopy systems.

Since the system allows for sophisticatedly deflecting or stressing the culturing membrane and the cells adhered thereto it allows for mimicking effects of biophysical factors from specific tissues microenvironment to predict the in-vivo response of a chemical compound or compositions, in humans or animals. It also allows investigating the pharmacokinetic behaviour of chemical compounds or compositions on a particular tissue or groups of tissues. The system can also be used to assess the systemic response of a chemical compound or compositions. Another application of this system is to test patients' own cells to tailor and optimize the therapeutic treatment for each patient.

By providing the docking station and the handling unit in the system, a comparably high modularity and flexibility can be achieved. Also the efficiency can be comparably high since the system allows for a simple real time handling and/or exchange of single components such as the culturing modules or the like.

In particular, the handling unit of the cell culturing system according to the invention allows on one hand to interact with the culturing module or a plurality thereof as well as on the other hand with the docking station as well. Beyond others, the handling unit can be established as a functional interface between the culturing module and the docking station. Thereby, it makes it possible that the actuation feeding channel of the docking station and the culturing well of the culturing module are functionally connected to each other via the actuation bore of the handling unit without requiring any tubing or the like. Like this, a pressure can efficiently be applied to the actuation layer via the docking station and the handling unit. Optionally, also other structures of the culturing module and the docking station are connected via channels or the like provided in the handling unit. For example, additional microchannels can be provided in order to transport a cell culture medium or the like. In any case, a microfluidic channel arrangement can be formed by the handling unit simply when the handling unit together with the culturing module is docket or placed in the docking station. Thus, the handling unit allows for tubelessly connecting the channels and wells of the culturing module and the docking station which can make handling of the system considerably easier.

More particularly, by equipping the bottom of the handling unit with the actuation bore and correspondingly equipping the docking station with the actuation feeding channel mating to the actuation bore the construction can be comparably simple and robust. In particular, it can be prevented that tubings have to be attached to the culturing module or the handling unit. Rather, the system allows to fixedly install the docking station and connect it to appropriate tubings or tubes and to arrange and rearrange the handling unit and the culturing module as desired without any cumbersome installation steps or the like. This allows for further increasing efficiency of the system, particularly when being applied in a larger context such as in an industrial application.

In preferred embodiment the cell culturing system comprises at least one further culturing module structurally identical to the culturing module, wherein the handling unit has at least one further seat for accommodating the further culturing module and a bottom with at least one further actuation bore associated to the culturing well of the further culturing module; and the docking station has a further actuation feeding channel, wherein, when the handling unit is held by the coupling structure in the predefined position, a first end of the further actuation feeding channel is connected to the further actuation bore and a second end of the further actuation feeding channel is connected to the connector. Thereby, the cell culturing system preferably further comprises at least one further actuation layer, wherein the further seat of the handling unit is arranged to accommodate the further actuation layer and the bottom is separated from the further culturing module by the further actuation layer. In such arrangements, the handling unit allows for particularly ease the handling of the plural culturing modules. Like this, a particularly efficient assay or simulation can be achieved.

One particularity of the system can be that one or plural microfluidic channels are formed between the bottom of the handling unit and the handling unit once the two parts are reversibly coupled to each other. To maintain the culturing module coupled to the handling unit they can be pressed together by either mechanical forces created by stressed springs such as beams or clips, magnetic, electro-magnetic forces or adhesion forces such as induced by double sided tapes.

The modular cell culturing system according to the invention and its preferred embodiments described above and below enables to mimic a mechanical stress induced by breathing movements, shear stress generated by blood, urine, feces, or other physiological fluid flows and mechanical stresses acting on gastro-intestinal barriers (peristaltic), the skin or other in-vivo barriers. It also allows to perfuse tissues from other organs and to study the pharmacokinetic and pharmacodynamic behavior of chemical compounds or compositions on specific tissues or group of tissues. Furthermore, it allows for conveniently controlling the flow of a medium inside the culturing well of the culturing module.

Further, the cell culturing system enables to investigate the complexity of interactions between different tissues or group of tissues from different organs. Instead of having only one culturing membrane, several culturing membranes or cell compartments can be integrated either in series or in parallel in the cell culturing module. The flow in each of these culturing chambers can be regulated by valves, made of the actuation layer and the cell culturing module, or of the actuation layer and the handling unit. The actuation layer can also be used to monitor the pressure and/or the flow inside the system. The flow in each tissue can, thus, be determined in order to reproduce in-vivo shear stress. Interactions between organs, for instance between the lung alveolar barrier and the liver, or a lung alveolar barrier-liver-breast cancer, or the lung and the lymphatic system, each combinations that take place in-vivo can thus be reproduced. Endothelial cells can cover the surfaces of all or part of microfluidic channels to reproduce blood vessels.

The culturing membrane can be either elastic or not. It can be a thin polymeric membrane, e.g., with a thickness between about 0.5 micrometer ($\mu m$) to about 200 $\mu m$ and with or without pores, typically of about 0.2 $\mu m$ to about 1000 $\mu m$. The membrane can be made of either elastic material such as Polydimethylsiloxane (PDMS), Polyurethane (PU), or the like, or a hard polymer, such as Cyclic Olefin Copolymer (COC), Polystyrene (PS), Polycarbonate (PC), Polypropylene (PP), Poly(methyl methacrylate) (PMMA) or the like, or a combination thereof to obtain a multilayer composition. It can be coated with extracellular matrix proteins such as laminin, collagen, elastin, fibronectin, or hydrogel, fibrin gel and the like or a combination thereof and reach a thickness of several millimeters. Cells can be cultured on both sides of the culturing membrane. The culturing membrane can also be made partly or completely with a support/scaffold with large pores filled with extracellular matrix proteins, such as collagen, elastin, laminin, fibronectin and the like or a combination thereof. The pores of the support/scaffold can typically be about 50 $\mu m$ to about 1000 $\mu m$, and have a circular, quadratic, rectangular, triangular, or the like shape, or a combination thereof.

Preferably, the culturing membrane comprises a mesh. In this specific embodiment, the culturing membrane or support/scaffold is provided with the mesh, whose thickness can be of a few micrometers, typically of about 1 $\mu m$ to about 100 $\mu m$. The mesh can be made of polymer, metal, glass, silicon and silicon nitride, silicon oxide, and the like, or from a biodegradable material. The distance between pores or holes can typically be about 2 $\mu m$ to about 200 $\mu m$. To mimic lung alveoli, the pores/holes of the mesh can have a preferred dimension of about 200 $\mu m$ to about 500 $\mu m$ in diameter close to the in-vivo dimensions. Thus, such a culturing membrane allows for mimicking in-vivo tissue such as lung alveoli tissue or similar in a comparably precise manner.

Even though in the present invention the culturing membrane with the mesh is used in the system according to the invention such culturing membrane can also be used in other systems. In particular, such culturing membrane is suitable and intended to be used in any system in which appropriate in-vivo tissue is to mimic particularly where cell culturing on such a tissue is to be mimicked.

The docking station can fulfill plural functions within the cell culturing system such as tightly coupling the handling unit to the docking station, e.g., using magnets, electro-magnets or springs, so that no air leakage occurs between these two parts, distributing the pressures generated by the control unit in the actuation feeding and, in some embodiments, other channels ending in holes located at the top of the docking station that align and connect with the bottom of the handling unit.

In an embodiment, the docking station and/or the handling unit can be equipped with supplementary functions aimed at monitoring the tissue metabolism and response to chemical compounds or compositions. For example, they can be equipped with one or more sensors and/or optical components, such as optical lenses or microscopy objectives coupled with digital cameras, to monitor in real time the changes of the tissues grown in the cell culture module or in the handling unit.

In another embodiment, impedimetric or optical sensors can be integrated in the docking station and/or in the handling unit. This allows for monitoring in real time the deflection of the actuation layer and of the culturing membrane. Furthermore, by means of such sensors a feedback loop can be integrated in the system in order to control the mechanical strain, to modify or maintain it, and/or to measure changes in the mechanical properties of the culturing membrane. Furthermore, optical sensors can be used to monitor oxygen, pH, $CO_2$ concentrations and other analytes in the culturing well.

In yet another embodiment fluidic access holes can be added at the bottom of the handling unit and corresponding fluidic channels in the docking station. Such channels and access holes may be used to deliver chemical compounds or compositions to the cell cultures in the handling unit or the culturing module. In a non-limiting example, such a channel may be used to evacuate the supernatant from the cell culture or to collect the supernatant for further analysis.

The docking station can comprise two assembled plates between which a sealing membrane or seal layer is sandwiched. The docking station can be made of materials that can be sterilized. Typical materials comprise PMMA, Polyoxymethylene (POM), PC, PS, or the like, whereas the materials of the sealing membrane and of a top sealing membrane can be PU, PDMS, or the like. To distribute the pressures created in the pressure control unit, the actuation and in some embodiments further channels are created in the docking station. An array of through holes can be produced in the sealing membrane, and in the top sealing membrane. They enable the air pressures transported through the channels to pressurize the actuation membrane. The top sealing membrane at the top of the docking station can ensure airtightness between the docking station and the handling unit.

The coupling structure of the docking station can be arranged to maintain the handling unit by mechanical forces. For example, springs can be used to maintain the handling unit tightly coupled to the docking station. Another possibility is to maintain airtightness between the two parts by applying a vacuum in cavities located between the handling unit and the docking station. Magnetic and/or electro-magnetic forces may additionally or alternatively be used to couple these two parts. For example, permanent magnets can be integrated in the handling unit and permanent or electromagnets in the docking station.

In an advantageous embodiment the docking station is arranged to couple plural handling units. In another embodiment, two docking stations are combined in a single arrangement with functions of both systems.

In another embodiment, the docking station can integrate the controller.

Via the coupling structure, the handling unit can be removably or reversibly coupled to the docking station and to its pressurizable actuation and in some embodiments further channels. The actuation and in some embodiments further bores located in the bottom of the handling unit aim at pressurizing the actuation and in some embodiments further wells of the culturing module and at actuating the actuation membrane at the bottom of the handling unit, i.e. at the bottom of the seat of the handling unit. Some main functions of the handling unit are arranging the culturing module or a plurality thereof in a predefined position and orientation, pressurizing the actuation and, possibly, further wells of the culturing module, actuating the actuation layer or membrane located at the bottom of the handling unit, and serving as cell culture substrate.

A preferred format of the handling unit can be that of a standard multiwell plate as mentioned above, but other dimensions are also possible. The handling unit can be made of a hard polymer, typically PS, COC, PP, PMMA, PC, or the like or soft polymers, such as PU, and can be injection molded, 3D printed or produced with standard milling and drilling techniques. It is associated to the actuation layer which can be irreversibly bonded to it, e.g., by plasma activation, glued, or thermally bonded to the topside of the handling unit.

The handling unit can be equipped with one single or plural seats in order that a desired number of identical or varying culturing modules can be reversibly coupled. Mechanical and/or magnetic forces can be used to couple the culturing modules and the handling unit. A preferred design can be to allow coupling two culturing modules on the handling unit.

In one embodiment, a layer of microelectrodes (Pt, Au, Ag, AgCl, C, Ti, Ta, . . . ) can be integrated on the handling unit either directly on it or between the handling unit and the actuation layer. The microelectrodes can be screen-printed, 3D printed, laminated, or created on a flexible printed circuit board (PCB) bonded on the handling unit. Such microelectrodes are intended to detect changes in the cell culture, or within the supernatant, or detect changes of the mechanical properties of the culturing membrane. These microelectrodes can be used to monitor a flow rate of the perfused cell culture media or changes of the cell culture in the handling unit or in the culturing module.

In a further embodiment, microstructures can be created in the handling unit, such as open microchannels, or microwells, or a porous scaffold for cell culture by modifying part of the bottom of the seat of the handling unit. This can be done by partly etching the bottom of the handling unit or the bottom of the seat of the handling unit.

The actuation layer can be made of an elastic and biocompatible material such as PDMS, PU, Styrene-Ethylene-Butylene-Styrene (SEBS) elastomers, or the like or a combination thereof, for instance in a multi-layer construct. It can serve plural purposes comprising: acting as an actuator when being suspended on top of the bore(s) or cavity/cavities at the bottom of the handling unit by, when the actuation or other bores are provided with a positive pressure, being deflected outside of the respective bore, and, when the actuation or other bores are provided with a negative pressure, being deflected in the respective bore; acting as a sealing and enabling to reversibly and tightly couple the cell culture modules; and being used as a cell culture substrate.

The actuation layer can be non-porous and can have a typical thickness of about 1 μm to about 200 μm. For conventional operations it can be about 100 μm thick. The recoil of such a thick actuation layer can enable it to retrieve its original non-actuated position fast and without the need of a supplementary pressure. When comparably small changes take place in the culturing module which need to be detected a comparably thin actuation layer can be used. As an example, such an actuation layer can be used for monitoring in real time changes of mechanical properties of the thin, porous and elastic culturing membranes integrated in the culturing module. Upon such modifications, the deflection of the membrane can vary and be detected. However, for this, the applied pressure on the actuation layer typically needs to be in the same order of magnitude than the pressure difference change induced by the membrane with altered mechanical properties. Furthermore, the actuation layer can be partly coated with scaffolding material for the cell culture such as hydrogel, fibrin, collagen, laminin, fibronectin or other scaffolding materials, or a combination thereof.

In the cell culturing system plural actuation layers can be integrated wherein they can be made of various thicknesses and of various materials. They may also include optical features, such as lenses, sensors and the like.

In application of the cell culturing system, the actuation layer can be used to create a peristaltic pumping between it and the culturing module. Thereby, the peristaltic movements can be created by deflecting the actuation layer in or out the actuation bore and/or other additional bores.

Preferably the culturing module has an inlet well and an outlet well, the bottom of the handling unit has an inlet bore and an outlet bore, wherein, when the culturing module is arranged in the seat, the inlet bore is associated to the inlet well and the outlet bore is associated to the outlet well, and the docking station has an inlet feeding channel and an outlet feeding channel, wherein, when the handling unit is held by the coupling structure in the predefined position, a first end of the inlet feeding channel is connected to the inlet bore, a first end of the outlet feeding channel is connected to the outlet bore, and each second end of the inlet feeding channel and the outlet feeding channel is connected to a connector.

Via the inlet and outlet feeding channels as well as the inlet and outlet bores the actuation layer can be positively or negatively deflected by changing the pressure conditions similarly as explained above in connection with the culturing well. Thereby, a flow path between the inlet well, the culturing well and the outlet well can be precisely opened or closed. The inlet and outlet bores together with the actuation layer and structures of the culturing module can function as valves. Like this, a flow can sophisticatedly be generated inside the culturing well.

For example, by adjusting the pressure in the inlet and outlet bores of the handling unit appropriately a constant flow can be generated through the culturing well. Like this, constant perfusion can be induced to mimic the blood flow.

Preferably, the cell culturing system comprises a pressure control unit with a pump arrangement, at least one port connected to the pump arrangement and a processor (CPU) for controlling the pump arrangement, such that at each of the at least one port pressure is individually adjustable. By means of such a pressure control unit the pressure in the actuation channel as well as also in the inlet channel and the outlet channel can be precisely be adjusted. Also, such control unit can allow for implementing variable pressure profiles automatically applied. For that purpose the processor can be programmable such that it suits to the conditions to be mimicked.

The pressure control unit advantageously has a number of individually adjustable ports corresponding to the number of connectors to be serviced. Also, a single pressure control unit can be associated to plural docking stations.

Furthermore, the cell culturing system preferably comprises a number of tubes, wherein each tube connects one of the ports of the control unit with one of the connectors of the docking station.

The pressure control unit or controller can be an electro-pneumatic system that is computer controlled with the CPU integrated. The pump arrangement can have one or plural pumps integrated in the controller. It can generate positive and negative pressures with either constant, cyclic or ramp profiles. Such profiles can be programmed in and controlled by the processor. The control unit can further comprise pressure sensors. The pressures that are controlled by means of the pressure sensors can be transmitted from the at least one port to the at least one connector of the docking station, e.g. via the tubes or tubings, and can be recorded by the CPU. The pressures generated by the controller can be typically used to create constant, cyclic or ramp pressure profiles to expose the tissues to different mechanical stimuli. In some embodiments it can further be used to open valves enabling the exchange or the sampling of the culture medium on the basolateral or basal side of the culturing membrane.

In one embodiment, the control unit or controller provides a cyclic pressure profile that mimics the physiological breathing movements of the lung. Typically, such movements comprise between 5% and 12% linear mechanical strain. It can also provide pathophysiological cyclic mechanical strain levels similar to those some patients are exposed to during ventilation, which may induce lung injuries. Such movements can involve more than 15% linear strain, often between 20 and 30%.

Advantageously, the control unit is equipped with additional electronic circuits to record and analyze electrical and/or optical signals obtained from sensors integrated in the docking station or integrated in the cell culturing module. As an example, electrodes may be integrated in the docking station, in the actuation layer and/or in the culturing module to monitor the trans-epithelial electrical resistance (TEER) of the tissue or the cell culture layer cultured on the culturing membrane. Optical sensors can be integrated in the docking station and/or the handling unit to monitor the deflection of the actuation membrane and/or of the culturing membrane. Furthermore, a synergy effect between the docking station, in which optical sensors can be located, and the handling unit and/or the culturing modules can be achieved. Any changes of the deflection of one of the membranes (following for instance a biological event in the culturing membrane) can indicate a potential change of the mechanical properties of one or both the actuation layer and the culturing membrane. A feedback loop can be created to compensate or note the loss or gain of mechanical strain levels in the layer or membrane.

Preferably, the cell culturing module has a cap arranged at a top of the culturing module which cap comprises a channel connected to the docking station via the culturing module and the handling unit and to the inlet well. Such a cap can allow for providing perfusion of the system.

Thereby, the cap of the cell culturing module preferably has a second channel connected to the docking station via the culturing module and the handling unit and to the outlet well. Like this, the perfusion can be controlled by the inlet and the outlet. This can be important when using a flexible membrane so that the perfusion does not deflect the membrane.

Thereby, the cell culturing module preferably comprises an actuation membrane arranged over the culturing well. This allows for creating compression on the cells or overpressure.

Preferably, the cell culturing module has a first culturing well with a first cell type and a second culturing well with a second cell type that are connected to each other with a channel located between the handling unit and the culturing module. Like this, a two-organs system can efficiently be provided.

Preferably, additional culturing wells are interconnected. Like this, a multi-organ system may efficiently be provided or established.

Preferably, the cell culturing system comprises a channel which connects two culturing wells at the apical side of the culturing membrane or at the basal side of the culturing membrane. In other words, two culturing wells can be connected with a channel located between the apical sides of the two culturing wells or two culturing wells can be connected with a channel located between the basal sides of the two culturing wells. Like this, specific connections between two organs can be provided which allows for improving the mimicking of in vivo conditions.

Preferably, the cell culturing system comprises a channel having a valve, wherein the channel connects the outlet well and the inlet well. For example, the cap of the cell culture module can comprise a channel that connects an outlet and an inlet, an anti-return valve and two tubings that plunge in the outlet and inlet. For example, a recirculation flow can be generated by means of the channel wherein the valve allows for a precise adjustment of the flow. Such arrangements allow for further improving the mimicking of in vivo conditions.

Preferably, the cell culturing system comprises a further docking station identical or similar to the docking station, a cell culture hood and an incubation hood, wherein the docking station is arranged in the culture hood and the further docking station is arranged in the incubation hood.

Thereby, the cell culture hood preferably comprises a culturing housing with an interior adapted to be sterile. Also, the incubation hood preferably has an incubating housing and conditioning structure adapted to adjust conditions in the interior of the housing.

Providing the cell culturing system with the two hoods allows for positioning the docking station or a plurality thereof in the cell culture hood and the further docking station or a plurality thereof in the incubation hood. The latter can typically be humidified at 37° C. and with an atmosphere containing about 5% $CO_2$. It can also be installed in a hypoxic or hyperoxic chamber. Main functions of such first and second docking stations are the same, they are duplicated to ease their use, and to avoid the need of disconnecting and reconnecting fluidic tubings, i.e. the tubes, to replace cell culture medium.

Preferably, the actuation bore of the bottom of the handling unit has a cavity section neighboring or being adjacent to the actuation layer, e.g., when the cell culturing module is arranged in the seat of the handling unit. Such a cavity section allows for predefining a maximum deflection of the actuation membrane.

For the same purpose, each of the inlet bore of the bottom of the handling unit and the outlet bore of the bottom of the handling unit preferably has a cavity section neighboring the actuation layer, e.g., when the cell culturing module is arranged in the seat of the handling unit.

Preferably, the handling unit comprises a lid for covering the culturing module arranged in the seat of the handling unit. Such a lid allows for keeping the module under sterile conditions. The lid or coverlid can close the handling unit and keep the environment in the handling unit sterile.

Preferably, the handling unit comprises a liquid reservoir. Such liquid or water reservoir or a plurality thereof can avoid or limit the evaporation of cell culture solutions in the system. The reservoir can contain several milliliters of solution, preferably sterile water or PBS.

Preferably, the cell culturing system comprises a station sealing layer attached to the handling unit or to the docking station and equipped with a through hole such that the station sealing layer is arranged between the handling unit and the docking station when the handling unit is held by the coupling structure of the docking station in the predefined position, wherein the first end of the actuation feeding channel is connected to the actuation bore via the through hole of the sealing layer. For example, the station sealing layer or membrane can be irreversibly bonded on a bottom side of the handling unit or on the top side of the docking station to guarantee a tight sealing between the docking station and the handling unit.

Also, the station sealing layer preferably has a further through hole and the first ends of the inlet feeding channel and the outlet feeding channel are connected to the inlet bore and the outlet bore via the further through holes of the sealing layer.

Preferably, the culturing module has an upper plate and a lower plate and the culturing membrane is arranged between the upper plate and the lower plate.

The culturing module and particularly its plates can typically be made of a hard polymer, such as PS, COC, PMMA, PC, PP, or the like, but can also be made of a soft polymer such as polyurethane, or the like. It can advantageously be injected molded or reaction injection molded but can also be 3D printed or produced with standard milling and drilling techniques. The culturing membrane can be bonded, e.g., by plasma oxygen on the lower plate but can also be bonded on the upper plate. The upper and lower plates with the culturing membrane sandwiched in between can be either reversibly or irreversibly bonded, e.g. using adhesive layers, glues, thermal bonding or plasma bonding or mechanical components such as clips or rivets. A cell culture module lid can optionally be placed at the top of the culturing module to pressurize specific wells. The design of this lid may differ to fit specific purposes. For example, it may include three-dimensional structures, such as an opening allowing for e.g. the delivery of cells, of cell culture medium or of drugs in the well or a system aimed at compressing tissue. The cell culture module lid can be made of injected molded polymer, such as PS, PP, PC, PMMA, and the like or a soft polymer such as polyurethane and the like, by injection molding or reaction injection molding or 3D printing of produced by standard milling and drilling. It and can be maintained on the top part of the culturing module by mechanical, magnetic or adhesion forces. Mechanical clips or permanent magnets maintain the two parts tightly to avoid any loss of air pressure in the inlet well and/or the outlet well. A sealing membrane that guarantees the airtightness between the cell culture module and its lid can be sandwiched between the two parts. It can be either reversibly or irreversibly bonded on the cell culture module lid or on the top part of the culturing module.

In an embodiment, the cell culture module lid can be structured with microchannels and can integrate valves. For this, a cavity covered by a flexible membrane can be structured in the lid which can be pressurized via an access hole connected to the docking station. In another embodiment, this lid can be replaced by a pierceable membrane that maintains the inlet and/or the outlet wells pressurized while the sampling and/or delivery of solutions or cells in the wells is still possible though the pierceable membrane. This can be done by using pipettes or needles that resist piercing the membrane.

In one embodiment, the culturing module contains an array of six independent microfluidic systems for cell culture applications. The six microfluidic systems can be each separated by 9 mm and can each comprise three aligned wells each equally separated by 9 mm. In particular, the three aligned wells can comprise an inlet well, a culturing well and an outlet well. The mentioned distance corresponds to the standards defined by the Society for Laboratory Automation and Screening (SLAS) for a 96-well plates and to the distance between two pipettes in a multipipettor or pipetting robots. When the culturing module is coupled to the handling unit several microfluidic channels and microwells can be created at the interface between those two parts. The inlet well, serving as reservoir for cell culture media, can be connected to a microchannel that leads to the basal culturing chamber via a valve formed by the deflection of the actuation layer and the structure of the culturing module. A second microchannel connects the basal culturing chamber with the outlet well via a second valve similar to the first one. The two valves are usually actuated in parallel and are either normally closed (NC) or normally open (NO). In a standard configuration, i.e. when the valves are closed, the culturing well and particularly its basal chamber can be a closed compartment. A third valve, located in the basal culturing chamber and made of the actuation layer and of a cavity beneath it, can serve at modifying the pressure inside the basal culturing chamber. It can be deflected in two directions, depending whether it is pressurized with a positive or a negative pressure.

To exchange the cell culture medium in the basal culturing chamber the mentioned two valves located at the entrance and at the exit of the basal culturing advantageously are open. Further, to perfuse a solution in the basal culturing chamber the two valves can be kept open.

On top of the culturing module, a cell culturing module lid can be reversibly bonded to close the inlet and/or the outlet wells. A small channel either created on the top part of the culturing module or its lid can connect the inlet and/or the outlet wells to the pressurized system of the docking station via an access hole. This allows pressurizing the solution in the inlet well which can create a flow in the basal culturing chamber.

In one embodiment, a bypass channel connects the outlet and the inlet well. This setting enables to create a recirculation fluid path. At various time intervals, the cell culture medium in the outlet well is transported to the inlet well by closing the valves on each side of the basal chamber, opening the valve of the bypass channel and pressurizing the outlet well with a positive pressure. The bypass channel is typically formed between the handling unit and the culturing module.

In a further embodiment, the bypass channel is created in the lid of the culturing module. Small tubings or needles integrated in the lid at each end of the channel plunge in the inlet and outlet wells. In a preferred setting, the tubing/needle at the outlet protrudes until the bottom of the outlet well, whereas the tubing/needle from the inlet well is much shorter.

The cell culturing system preferably comprises a module sealing layer arranged between the upper plate and the lower plate of the culturing module and equipped with through holes such that the inlet well, the outlet well and the culturing well extend though the module sealing layer via its through holes.

The upper plate and the lower plate can be reversibly bonded, e.g., by using rivets that can be broken after use with a slight overpressure. An adhesive layer can also be used to reversibly bond the two parts. This enables the observation of the tissues or cells cultured on the culturing membrane in close proximity at high magnification using for instance oil objectives.

In one embodiment, two adjacent culturing chambers are connected with each other to enable the communication between tissues from those chambers. A channel can be created in the culturing module, either below or above the culturing membrane or a combination thereof. The channel can for instance be filled with gel, such as fibrin, fibrinogen, collagen, and the like, in which case an access port is required to introduce the gel from the top of the culturing module. The gel is maintained in the channel by surface tension. The channel can also be filled with a porous material such as polysulfone, polyurethane and the like.

In one embodiment, a valve formed between the handling unit and the culturing module is located between two basal chambers, either to stop the communication between tissues from adjacent culturing chambers or to regulate the flow in the basal chamber. It is also envisaged to bypass a basal chamber with an additional channel to limit the flow rate in a basal chamber.

Another aspect of the present disclosure relates to a method of culturing cells on a culturing membrane (culturing method). This method comprises the steps of obtaining a cell culturing system as described above; seeding cells on the culturing membrane in the culturing well of the culturing module; incubating the cells on the culturing membrane of the culturing module; arranging the culturing module in the seat of the handling unit; applying a cell culture medium into the culturing well of the culturing module; coupling the handling unit to the docking station; and adjusting a pressure in the actuation feeding channel of the docking station.

The method according to the invention allows for efficiently using the cell culturing system described above and thereby implementing the effects and benefits mentioned above in connection with the system and its preferred embodiments.

By adjusting the pressure in the actuation feeding channel, the pressure in the actuation bore of the bottom of the handling unit is accordingly adjusted. Like this, an over-or under pressure is applied to the actuation membrane which causes the actuation membrane to positively or negatively deflect. This, in turn, causes the culturing membrane do be deflected correspondingly.

For adjusting the pressure, the connector of the docking station can be connected to the port of the pressure control unit described above, e.g. via a tube.

In an embodiment of the method, the inlet and/or the outlet wells of the culturing module are pressurized, e.g., by a pressurized system of the docking station via an access hole. This allows pressurizing the solution in the inlet well which can create a flow in the basal culturing chamber of the culturing module.

In another embodiment of the method the culturing module is equipped with an elastic culturing membrane and a positive pressure in the inlet well is equivalent to a negative pressure in the outlet well. This allows for avoiding the deflection of the culturing membrane during the flow. In this configuration, the cells cultured on the culturing membrane can be cyclically stressed in three dimensions and perfused, i.e. exposed to shear stress and cyclic stress. The method or the culturing module can enable, thus, to recreate the mechanical stress induced by the breathing movements, the shear stress generated by the blood flow and other mechanical stresses acting on gastro-intestinal, the skin or other organs. It also allows studying the pharmacokinetic and pharmacodynamic behavior of chemical compounds or compositions on specific tissues or group of tissues.

Preferably, the method comprises a step of adjusting a pressure in the inlet feeding channel in order to open and close the inlet well towards the culturing well and a pressure in the outlet feeding channel in order to open and close the outlet well towards the culturing well. For adjusting the pressure, the further connectors of the docking station can be connected to the ports of the pressure control unit described above, e.g. via tubes.

Preferably, the cells are seeded on the culturing membrane when the handling unit is coupled to the docking station positioned in the cell culture hood and the cells are incubated on the culturing membrane when the handling unit is coupled to the further docking station positioned in the incubation hood.

Preferably, before coupling the handling unit to the further docking station it is covered by the lid.

Preferably, seeding and incubating the cells on the culturing membrane in the culturing well of the culturing module comprises seeding and incubating the cells on a first side of the culturing membrane in the culturing well of the culturing module, flipping the culturing module around and seeding and incubating the cells on a second side of the culturing membrane in the culturing well of the culturing module.

In one embodiment the method comprises configuring the cell culturing system to mimic the operation of lung alveoli. Lung endothelial cells can be cultured on the basolateral side of the culturing membrane, while lung epithelial cells can be cultured on the apical side of the culturing membrane. The lung alveolar barrier, i.e. the culturing membrane, can be cyclically stressed either at a physiological or pathophysiological levels. To be even more realistic, a culturing membrane made of components found in the basal membrane, such as collagen, elastin, and the like, is produced by using an ultra-thin mesh with pores/holes with dimensions similar to the size of alveoli, typically 200 µm to 300 µm. To create such a culturing membrane, a solution for instance of elastin and collagen is pipetted on the mesh, where it spreads in a homogeneous thin layer by surface tension. Usually the membrane is dried prior to be used. Before use, it is hydrated again, and cells are cultured on the membrane. Electrospinning of components found in the basal membrane can also be used to create the culturing membrane. Upon the presence of an under pressure, created by the actuation layer, the alveoli from the array deflect in three dimensions. The deflection of the culturing membrane in function of a given and known positive or negative pressure can be monitored in function of the time. Changes on the cell layers either on the apical or the basal side of the culturing membrane or both can be detected by a change in the deflection or optically using, e.g., FRET probes.

Changes of the culturing membrane stiffness, of the transient response of the culturing membrane during the elastic recoil, of the thickness of the culturing membrane or of a combination thereof can be detected by sensors such as impedimetric or optical sensors. These changes may result from modifications in the tissues, following for instance cell proliferation or cell death, wound injury, cell layer confluency, extracellular matrix production (typically but not limited to collagen), themselves induced by chemical compounds or composition of compounds exposure.

Thereby, changes of one or several of these parameters can be correlated to changes in lung functions observed in clinical parameters obtained for instance via spirometry, in patients suffering for instance of lung fibrosis, COPD or lung emphysema. Such correlation is very important, as it will ultimately enable to predict the effects of a compound or compositions for patients, whose cells or tissues can be tested on the modular cell culture system.

BRIEF DESCRIPTION OF THE DRAWINGS

The cell culturing system according to the invention and the method according to the invention are described in more detail herein below by way of exemplary embodiments and with reference to the attached drawings.

DETAILED DESCRIPTION

In the following description certain terms are used for reasons of convenience and are not intended to limit the invention. The terms "right", "left", "up", "down", "under" and "above" refer to directions in the figures. The terminology comprises the explicitly mentioned terms as well as their derivations and terms with a similar meaning. Also, spatially relative terms, such as "beneath", "below", "lower", "above", "upper", "proximal", "distal", and the like, may be used to describe one element's or feature's relationship to another element or feature as illustrated in the figures. These spatially relative terms are intended to encompass different positions and orientations of the devices in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. The devices may be otherwise oriented (rotated 90 degrees or at other orientations), and the spatially relative descriptors used herein interpreted accordingly. Likewise, descriptions of movement along and around various axes include various special device positions and orientations.

To avoid repetition in the figures and the descriptions of the various aspects and illustrative embodiments, it should be understood that many features are common to many aspects and embodiments. Omission of an aspect from a description or figure does not imply that the aspect is missing from embodiments that incorporate that aspect. Instead, the aspect may have been omitted for clarity and to avoid prolix description. In this context, the following applies to the rest of this description: If, in order to clarify the drawings, a figure contains reference signs which are not explained in the directly associated part of the description, then it is referred to previous or following description sections. Further, for reason of lucidity, if in a drawing not all features of a part are provided with reference signs it is referred to other drawings showing the same part. Like numbers in two or more figures represent the same or similar elements.

Figure 1:
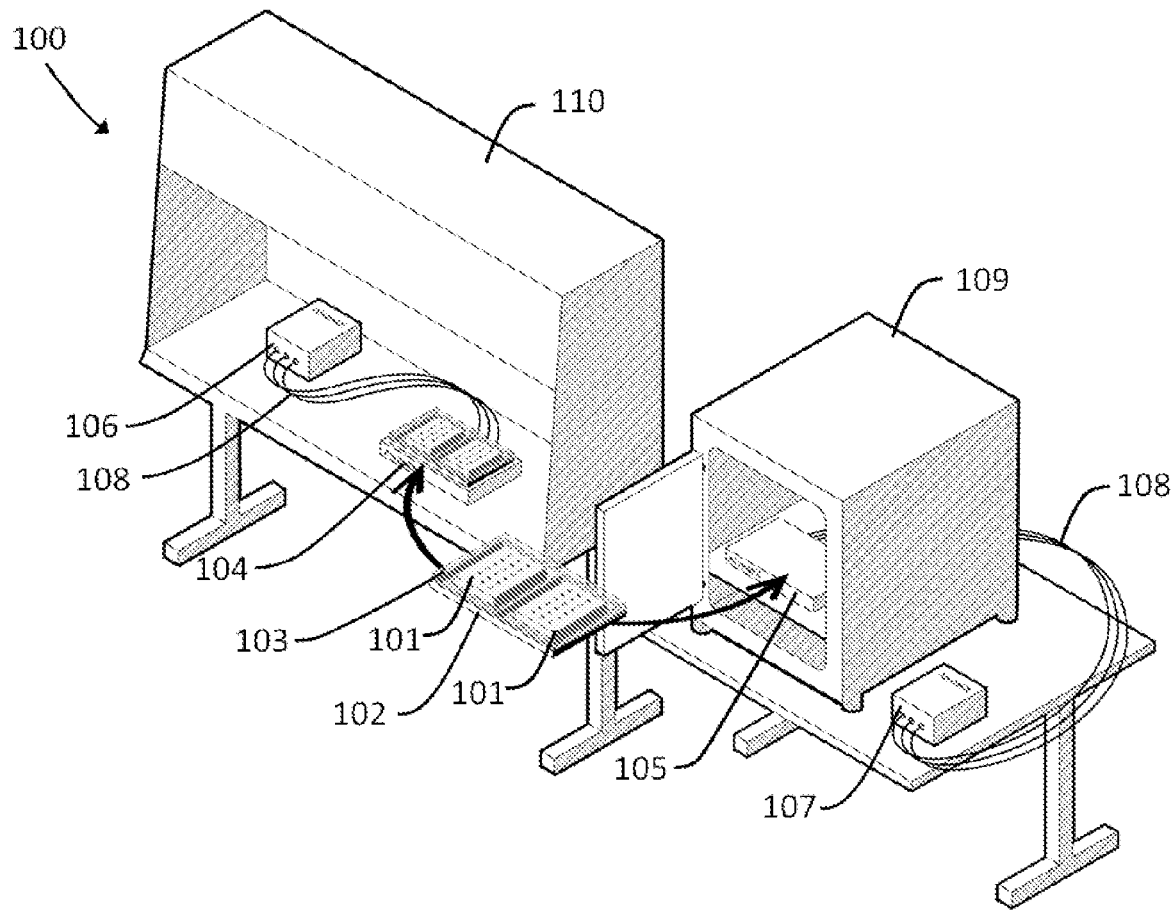
FIG. 1 illustrates an overall perspective view of a first embodiment of a cell culturing system according to the invention which is intended for in-vivo modeling tissue of organs in a standard laboratory setting.

FIG. 1 shows an overview an in-vitro cell culturing system 100 as a first embodiment of a cell culturing system according to the invention. The cell culturing system 100 is intended for modelling tissue of organs. It comprises a first controller 106 and a second controller 107 as control units. The first controller 106 is located inside a sterile environment formed by a cell culture hood 110. The second controller 107 is located next to a bioreactor as an incubation hood 109. The controllers have ports which are connected to a first docking station 104 and a second docking station 105 via fluidic tubings 108 as tubes. As the need may be, the tubings 108 can also comprise electrical wires, optical fibers or a combination thereof.

In connection with tissue of organs, the cell culturing system 100 has consumable parts which are composed of a handling unit 102, a coverlid 103 and multiple culturing modules 101. The consumable parts can be moved freely between the sterile environment, i.e. the cell culture hood 110, and the bioreactor, i.e. the incubation hood 109. The cell culturing system 100 comprises the first docking station 104 installed in the cell culture hood 110 and the second docking station 105 installed in the incubation hood 109. In each hood 108,109 the assembled consumable parts are coupled to one of the docking stations 104/105 and connected to the first and second controllers 106, 107 via the tubings 108. The consumable parts are placed above the docking station 104 and secured by means of a locking mechanism as shown below. This allows to perform cell manipulations, e.g. cell seeding, medium exchange and so on, in the cell culture hood 110 and cell culturing inside the incubation hood 109, similar to standard in-vitro systems. In the incubation hood 109, the cells can be mechanically stimulated.

Figure 2:
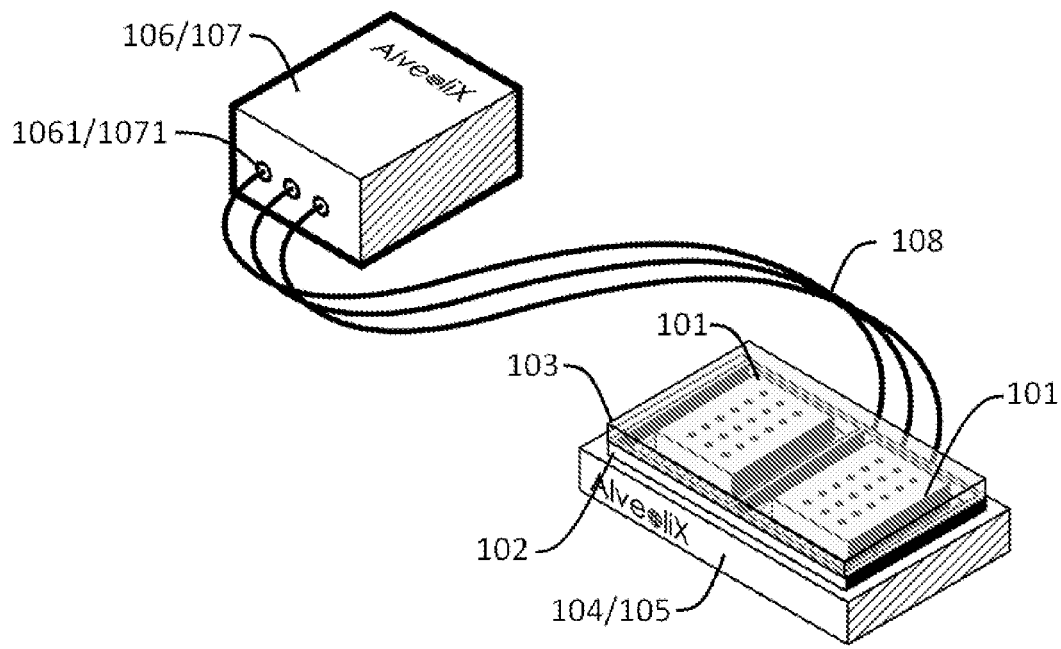
FIG. 2 illustrates a perspective view of a control unit, a docking station, a handling unit and culturing modules of the cell culturing system of FIG. 1.

FIG. 2 shows the setup of the first and second docking stations 104/105 together with the first and second controllers 106/107 in more detail. The first controller 106 comprises three ports 1061, an electro-pneumatic pump arrangement and a processor for controlling the pump arrangement. The pump arrangement and the processor are housed in the interior of the first controller 106 such that they are not visible in the FIG. 2. The controller is arranged to control the pumping arrangement such that at each of the ports 1061 a pressure is individually adjustable. The second controller 107 is similarly embodied as the first controller 106 and also comprises three ports 1071, a pumping arrangement and a processor. The first and second controllers 106/107 are connected to the respective first and second docking stations 104/105 via the tubings 108.

The controllers 106, 107 are used to define and control specific actions such as stretching, medium exchange, perfusion and so on, via connections 108, docking station 104 and coverlid 103 as lid.

Figure 3:
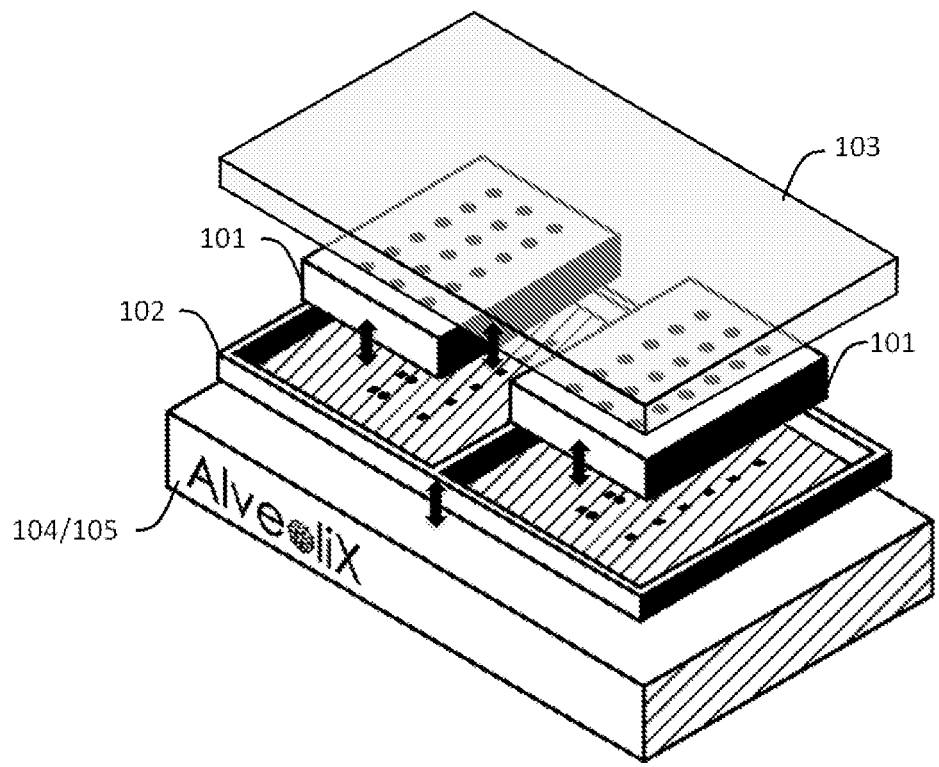
FIG. 3 illustrates a perspective view the docking station, the handling unit and the culturing modules of the cell culturing system of FIG. 1.

As can be seen in FIG. 3 the handling unit 102 can releasably be coupled to the first and second docking stations 104/105. The handling unit 102 is embodied to releasably accommodate two culturing modules 101.

The docking stations 104/105 are used to transfer the actuation from the controllers 106/107 and connections 208 to the handling unit 103. The handling unit 103 further transfers the actuation to the culturing modules 101, where the final action takes place. As a consequence, the action inside the culturing modules 101 is only taking place once the consumable parts are locked to the docking station 104/105. The culturing modules 101, the handling unit 102 and the coverlid 103 can be assembled and re-assembled reversibly as illustrated in FIG. 3. This means the handling unit 102 can be lifted and connected from and to the docking station 104, the culturing modules 101 from and to the handling unit 102 and the coverlid 103 from and to the handling unit 102.

Figure 4:
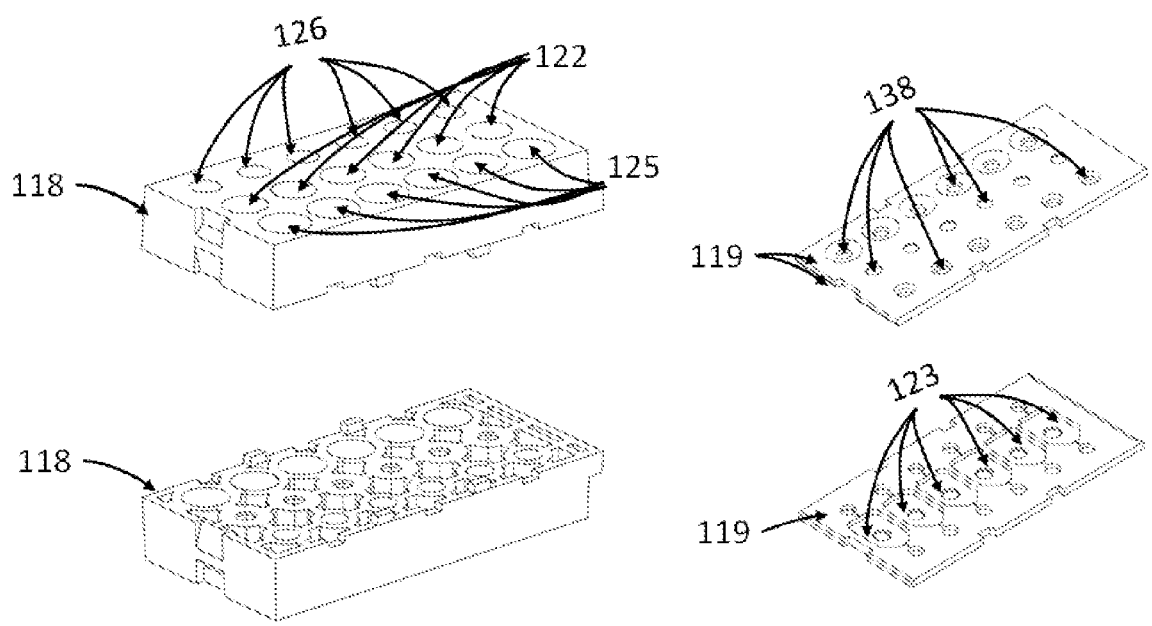
FIG. 4 illustrates a perspective view of one of the culturing modules of the cell culturing system of FIG. 1 in a disassembled state.

FIG. 4 illustrates some parts of the culturing modules 101. On the left side an upper plate 118 is shown top down and bottom up. The upper plate 118 has an essentially rectangular base shape and comprises a series of six apical culturing chambers 122 which are centrally arranged in a straight row in the upper plate 118. Parallel to the apical culturing chambers 122 a series of six inlet wells 125 and a series six outlet wells 126 are arranged. Each of the apical culturing chambers 122 is arranged between one of the inlet wells 125 and one of the outlet wells 126.

On the right side of FIG. 4 a lower plate 119 of the culturing module 101 is shown top down and bottom up. The lower plate 119 also has an essentially rectangular base shape which corresponds to the base shape of the upper plate 118. It is equipped with a series of six basal culturing chambers 123 which are identically positioned as the apical culturing chamber 122 of the upper plate 118. Adjacent to each of the basal culturing chambers 123, the inlet wells 125 and the outlet wells 126 a through hole 138 is provided in the lower plate 119.

The upper plate 118 and the lower plate 119 are made of a hard plastic material such as, e.g., PS, PP, COC, PMMA or the like. They can also be made of a soft polymer, such as polyurethane or the like.

Figure 5:
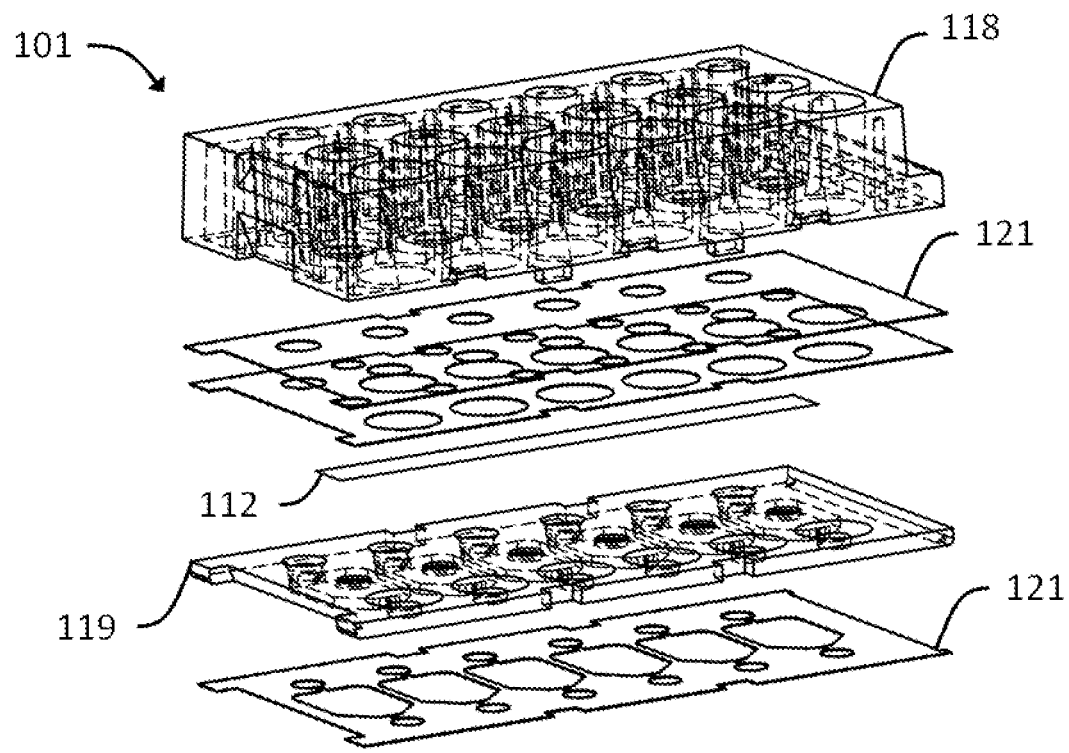
FIG. 5 illustrates a perspective exploded view of one of the culturing modules of the cell culturing system of FIG. 1.

As can be seen in FIG. 5 showing the culturing module 101 in an exploded perspective view, the culturing module 101 comprises a culturing membrane 112 and a module sealing layer 121 between the upper plate 118 and the lower plate 119. Additionally, it has a further module sealing layer 121 arranged below the lower plate 119.

Figure 6:
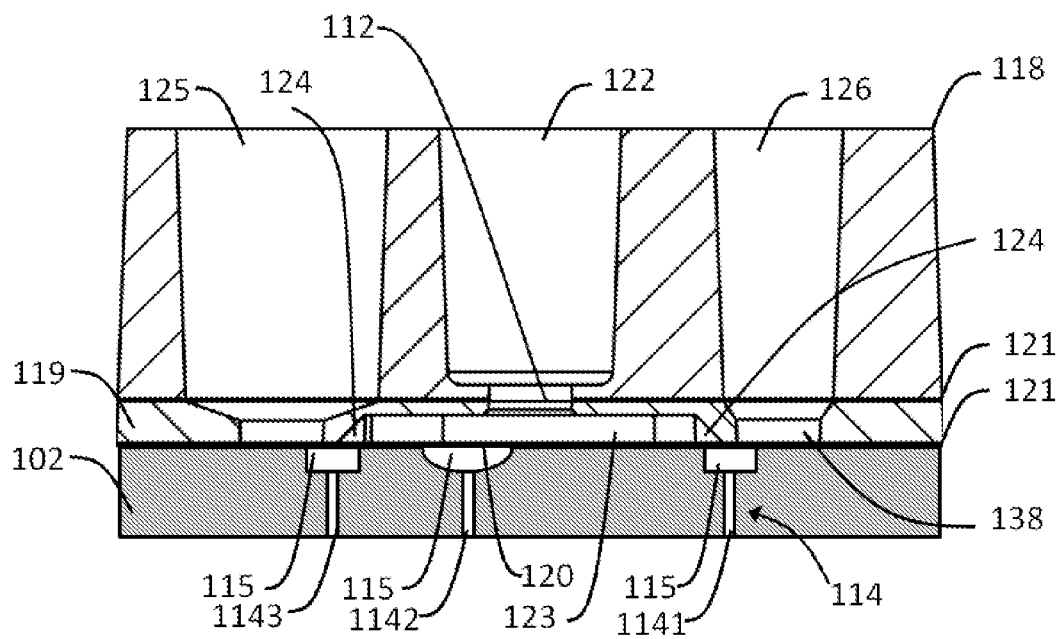
FIG. 6 illustrates a cross sectional view of the culturing module of the cell culturing system of FIG. 1 reversibly coupled to the handling unit showing one independent microfluidic system.

FIG. 6 shows the culturing module 101 in a cross sectional view when being assembled and coupled to the handling unit 102. The culturing membrane 112 and one of the module sealing layers 121 are sandwiched between the upper plate 118 and the lower plate 119. Thereby, the culturing membrane 112 separates culturing wells of the culturing module 101 into the apical culturing chamber 122 and the basal culturing chamber 123. Between the lower plate 119 and the handling unit 102 the other module sealing layer 121 and the actuation layer 120 are sandwiched. The handling unit 102 is equipped with thirty-six bores 114 extending vertically though the handling unit 102. The bores 114 are grouped in a straight row of twelve actuation bores 1141, a straight row of twelve inlet bores 1142 and a straight row of twelve outlet bores 1143. Each of the actuation bores 1141 is associated and neighbouring one of the basal culturing chambers 123, each of the inlet bores 1142 to one of the inlet wells 125 and each of the outlet bores 1143 to one of the outlet wells 126. Towards their top ends the bores 114 have a cavity 115 as cavity section.

Each of the inlet wells 125 and of the outlet wells 126 is connected to its neighbouring basal culturing chamber 123 by a microfluidic channel 124. Below each microfluidic channel 124 one of the cavities 115 of the inlet bores 1142 and the outlet bores 1143 are arranged. Together with the actuation layer 120 these cavity 115 form a normally closed (NC) valve. In order to open the valve and the respective microfluidic channel 124 an under-pressure is generated in the respective cavity 115 such that the actuation layer 120 is deflected into the cavity 115. Like this, the microfluidic channels 124 can individually be opened and closed by the one of the first or second controllers 106/107 adjusting the pressure.

In use of the cell culturing system 100, cells are first seeded in the culturing modules 101 in the cell culture hood 110. When cells are cultured on both sides of the culturing membrane 112, the culturing module 101 is flipped by 180° with the basolateral side of the culturing membrane 112 facing up. The cells are seeded on the culturing membrane 112 and incubated until they adhere. The culturing module 101 is flipped again by 180° so that the basolateral side of the culturing membrane 112 faces the handling unit 102. The culturing module 101 is then reversibly coupled to the handling unit 102. Subsequently, the basal culturing chamber 123 is filled with cell culture medium. This is done by reversibly coupling the handling unit 102 to the docking station first docking station 104 in the cell culture hood 110. Then, cells can be seeded on the apical side of the culturing membrane 112. The handling unit 102 is then reversibly coupled to the second docking station 105 situated in the incubator 109.

To exchange the cell culture medium, typically after 24 h or 48 h, the handling unit 102 is transferred to the first docking station 104 in the cell culture hood 110. Cell culture medium is exchanged on the apical side of the culturing membrane 112 like in a standard well plate. To exchange the cell culture medium in the basal culturing chamber 123, the inlet well 125 is filled with medium and outlet well 126 is emptied. The two valves located at the entrance and exit of the basal culturing chamber 123 are open and the medium is exchanged by the action of hydrostatic and surface tension forces. The medium collected in the outlet well 126 can be pipetted and analysed.

Once this operation is achieved, the coverlid 103 is placed on top of the handling unit 102 to maintain the environment in the handling unit 102 sterile. The handling unit 102 containing the culturing modules 101 and the coverlid 103 is then transferred to the incubator 109, where it is reversibly coupled to the respective second docking station 105. The cells can then be cultured under perfused condition at various flow rates, under mechanical compression or tension, or under a combination thereof. The electro-pneumatic second controller 107 connected to the second docking station 105 generates the required pressures to induce either the perfusion or the mechanical stresses or a combination thereof. After a specific time period, typically 24 or 48 hours the culturing modules 101 are transferred to the cell culture hood 110 to replace the cell culture medium or to expose the tissues to chemical compounds or compositions, or to sample the cell culture medium for analysis, or to test tissues cultured in the culturing modules 101.

Figure 7:
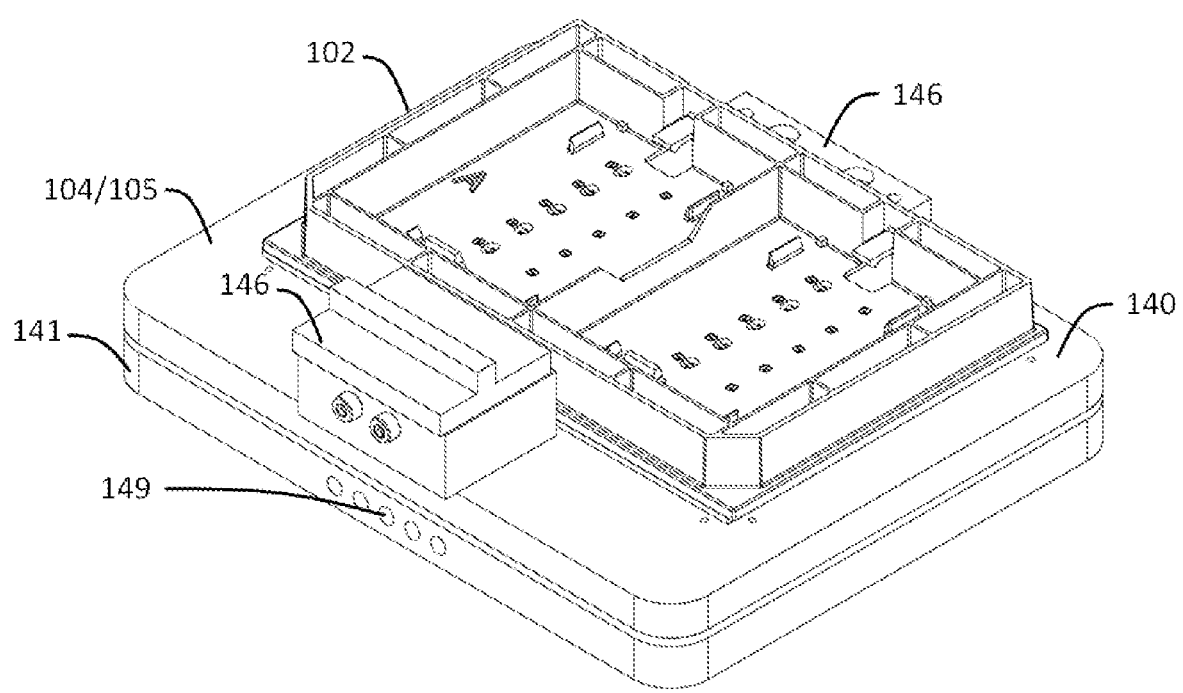
FIG. 7 illustrates a perspective view of the handling unit of the cell culturing system of FIG. 1 reversibly coupled to the docking station.

FIG. 7 shows a perspective view of the first and second docking stations 104/105 and the handling unit 102 of the cell culturing system 100. The first and second docking stations 104/105 are identically embodied with a top plate 140 and a bottom plate 141. At its edge the bottom plate 141 comprises a number of connectors 149 for being connected to one of the first and second controllers 106/107 via tubings 108. At its top surface the top plate 140 is equipped with a coupling structure 146 allowing to firmly hold the handling unit 102.

Figure 8:
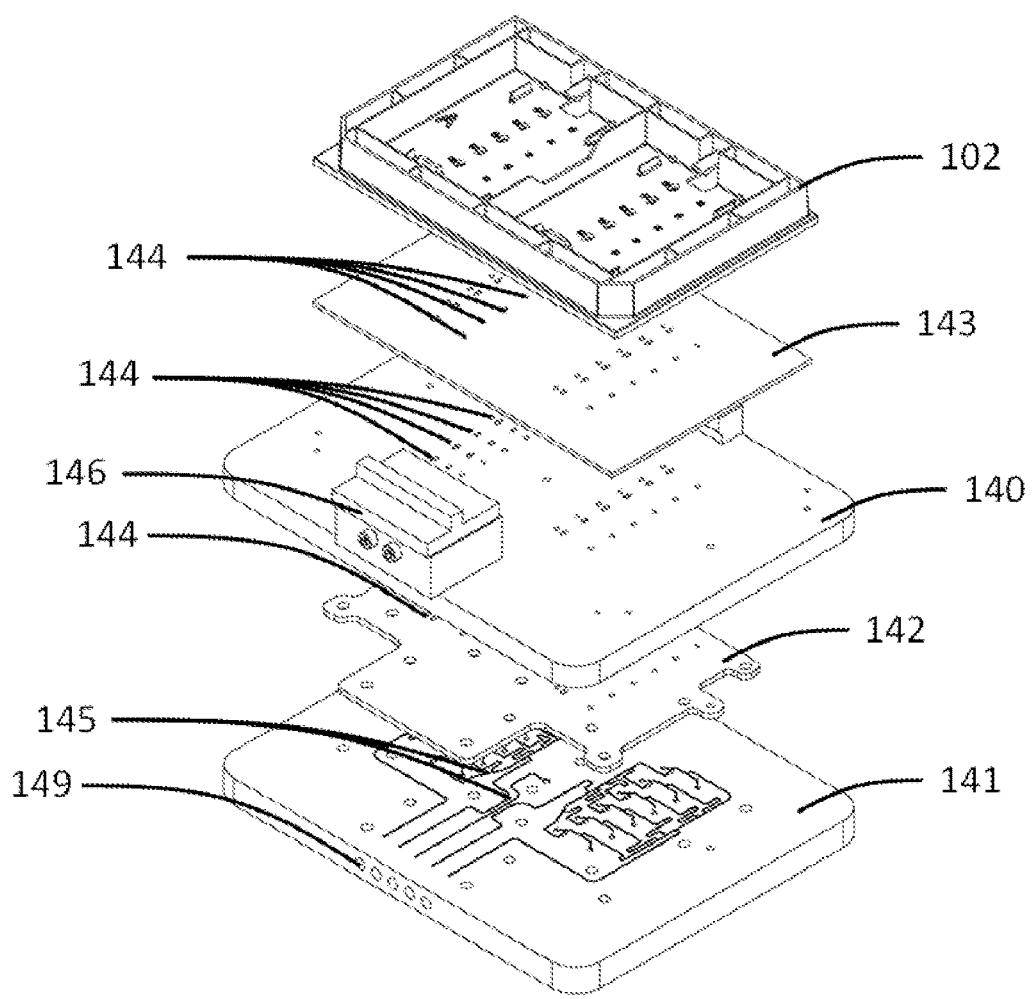
FIG. 8 illustrates a perspective exploded view of the handling unit and the docking station of the cell culturing system of FIG. 1.

In FIG. 8 the first and second docking stations 104/105 are shown in an exploded view. Thereby, it can be seen that they are equipped with a network of feeding channels comprising inlet feeding channels, outlet feeding channels and actuating feeding channels. Each of these channels comprises a horizontal section 145 provided in the bottom plate 141 and a vertical section 144 extending through a lower station sealing layer 142 covering the bottom plate 141, the top plate 140 and an upper station sealing layer 143 bonded to the top surface of the top plate 140. Each inlet feeding channel or the vertical section 144 thereof ends below one of the inlet bores 1142 of the handling unit 102, each actuation feeding channel below one of the actuation bores 1141 and each of the outlet feeding channels at one of the outlet bores 1143. The horizontal sections 145 of the feeding channels end at one of the connectors 149.

Figure 9:
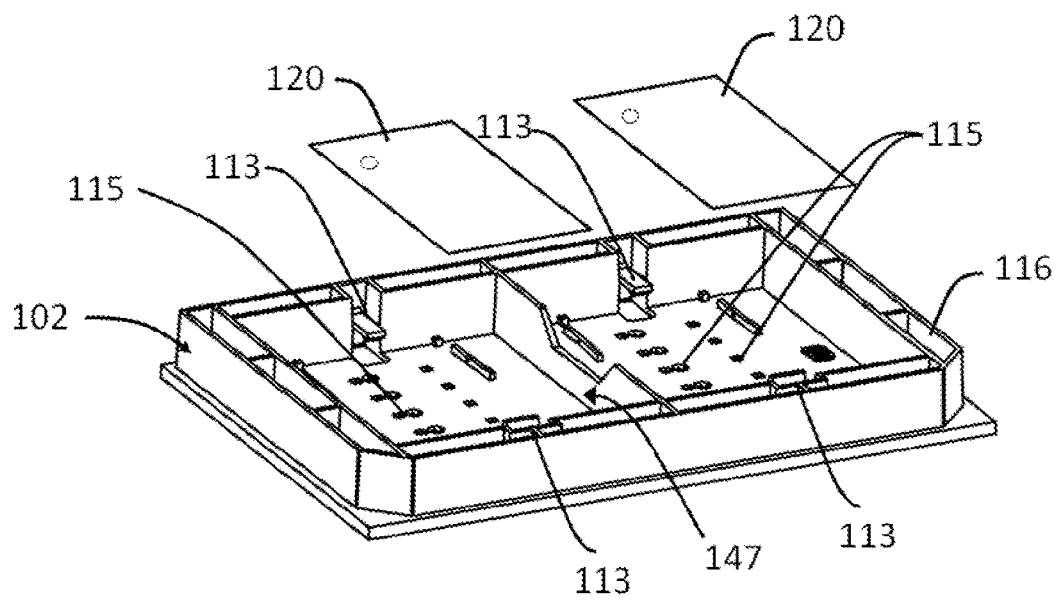
FIG. 9 illustrates a perspective view of the handling unit and two actuation layers of the cell culturing system of FIG. 1.

FIG. 9 shows the handling unit 102 of the cell culturing system 100 in more detail. It comprises two seats 147 separated from each other in each of which one culturing module 101 can be accommodated. At its lateral and longitudinal sides the handling unit 102 is provided with water reservoirs 116. At its longitudinal sides the handling unit 102 has clips 113 for fixing or holding the culturing modules 101. At the bottom surface of the seats 147 the cavities 115 are formed as described in more detail above. In each one of the seats 147 an actuation layer 120 is laid on, bonded to or attached to the bottom surface of the seats 147. When arranged in the seats 147 the actuation layers 120 cover the cavities 115.

Figure 10:
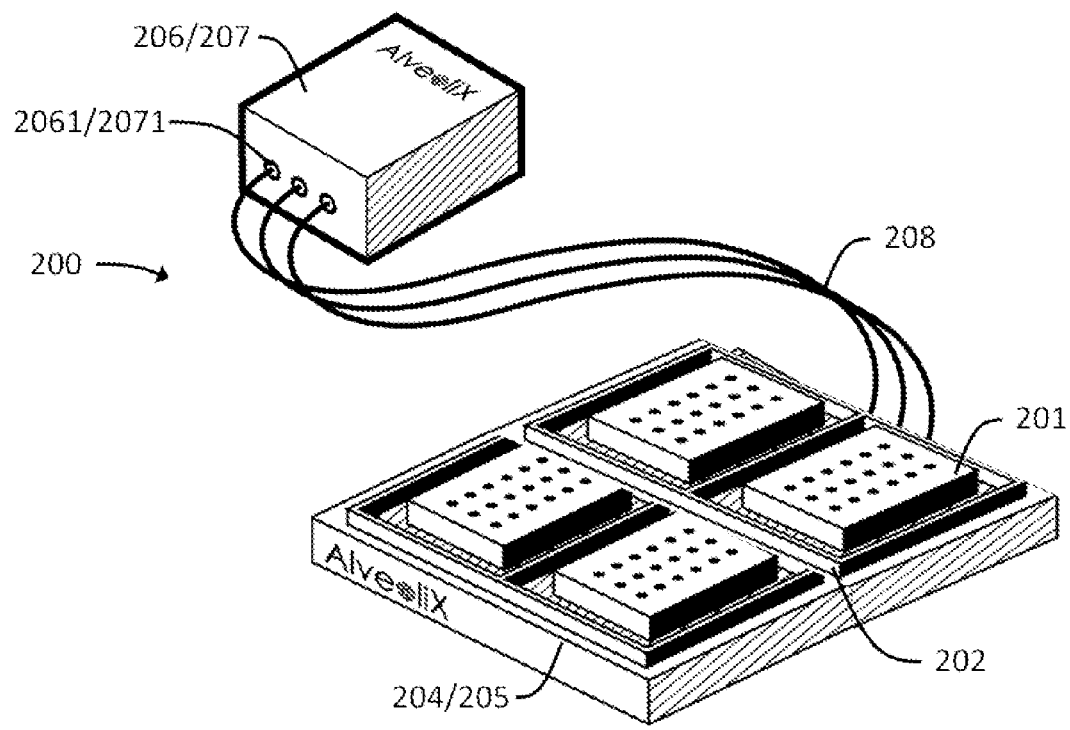
FIG. 10 illustrates a schematic of a docking station with two handling units each carrying two culturing modules of a second embodiment of a cell culturing system according to the invention.

In FIG. 10 a second embodiment of a cell culturing system 200 according to the invention is shown. The cell culturing system 200 is identically embodied as the cell culturing system 100 described above with the exception of what is explicitly mentioned in the following. A first docking station 204 and a second docking station 205 are connected to a first controller 206 and a second controller 207, respectively. The first or second controller 206/207 comprises three ports 2061/2071. The docking stations 205/206 are provided with coupling structures adapted to hold two handling units 202 wherein each handling unit 202 is embodied with two seats for accommodating two culturing modules 201. The docking stations 204/205, thus, allow for receiving four culturing modules 201.

Figure 11:
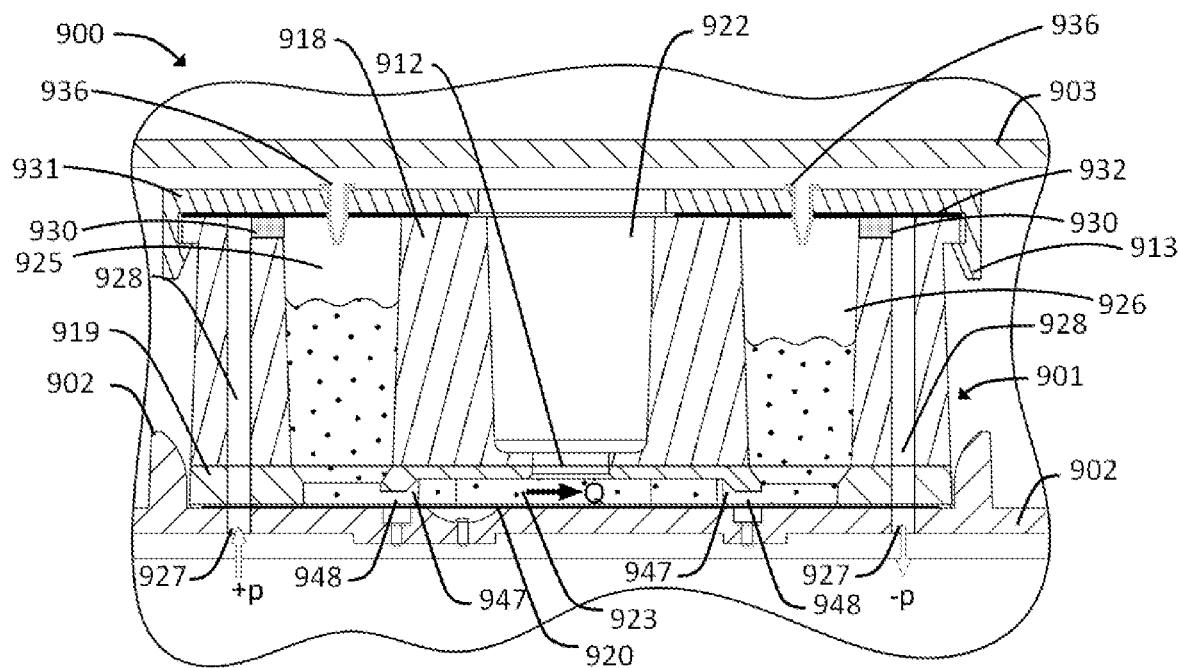
FIG. 11 illustrates a cross sectional view of a perfused culturing module coupled to a handling unit of a third embodiment of a cell culturing system according to the invention with a pierceable membrane bonded on the culturing module.

FIG. 11 shows a culturing module 901 of a third embodiment of a cell culturing system 900 according to the invention in a cross sectional view when being assembled and coupled to a handling unit 902. A culturing membrane 912 is sandwiched between an upper plate 918 and a lower plate 919 of the culturing module 901. Thereby, the culturing membrane 912 separates cell culturing wells into an apical culturing chamber 922 and a basal culturing chamber 923. Between the lower plate 919 and the handling unit 902 an actuation layer 920 is sandwiched. Inlet wells 925 and outlet wells 926 are connected to their neighbouring basal culturing chamber 923 by a microfluidic channel 924. Below each microfluidic channel 924 a normally open (NO) valve 948 is arranged.

The culturing module 901 mounted on the handling unit 902 is covered by a coverlid 903. For continuous perfusion additional features, to the ones mentioned above, are included but not limited to: access holes 927 in the handling unit 902, vertical channels 928 in the culturing module 901, a hermetic access port 936, a cap 931 holding the sealing layer 932 and filters 930. The continuous perfusion, indicated by the black arrow and Q-dot, is created by applying positive and negative pressure, controlled by controllers, the access holes in the handling unit 902 and the channels 928 in the culturing module 901, to the inlet well 925 and outlet well 926, respectively. Due to the cap 931 the pressure is contained in the system and a continuous flow can be generated. The filters 930 are used to avoid the entering of fluid, e.g., cell culture medium inside the channels 928. Therefore the filters 930 are permeable for one fluid such as air used for the actuation but impermeable for another fluid. To initially fill in the other fluid inside the culturing module 901, either via hermetic access ports 936 integrated in the cap 931 or the cap 931 is placed on the culturing module 901 after filling. The fluid in the outlet well 926 can be extracted similarly, hermetic access ports 936 or after removing the cap 931. Like this, the culturing module 901 can provide for an integrated continuous perfusion concept.

Figure 12:
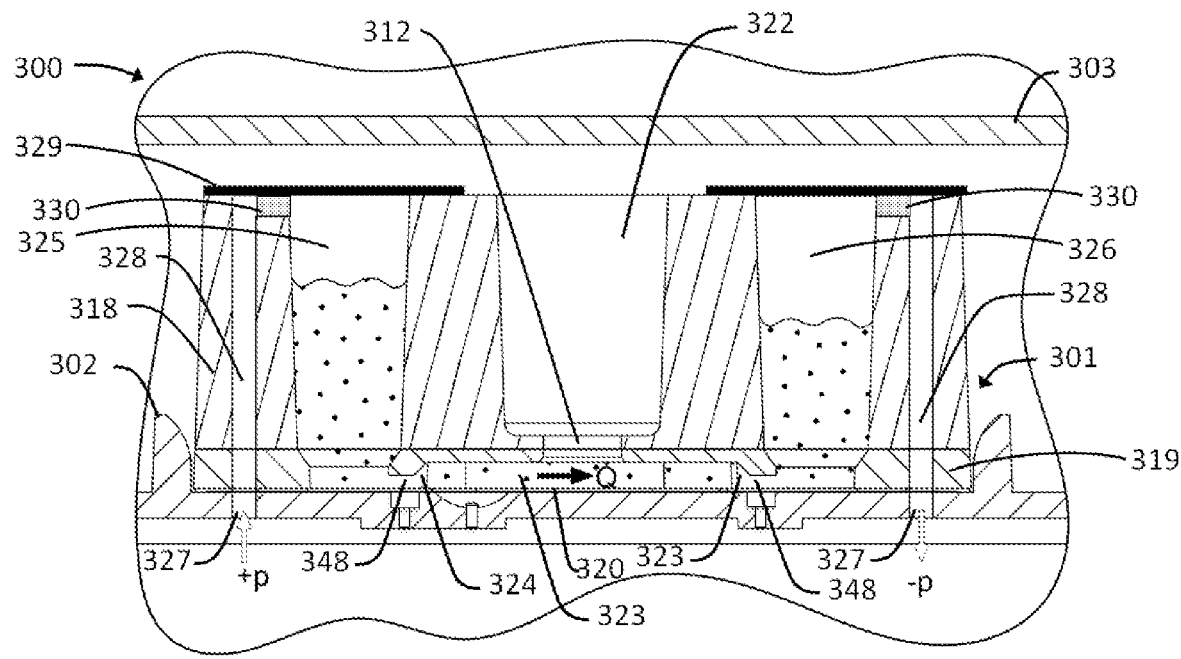
FIG. 12 illustrates a cross sectional view of a perfused culturing module coupled to a handling unit of a fourth embodiment of a cell culturing system according to the invention with a pierceable membrane bonded on the culturing module.

In FIG. 12 a culturing module 301 of a fourth embodiment of a cell culturing system 300 according to the invention is shown in a cross sectional view when being assembled and coupled to a handling unit 302. A culturing membrane 312 is sandwiched between an upper plate 318 and a lower plate 319 of the culturing module 301. Thereby, the culturing membrane 312 separates actuation wells into an apical culturing chamber 322 and a basal culturing chamber 323. Between the lower plate 319 and the handling unit 302 an actuation layer 320 is sandwiched. Inlet wells 325 and outlet wells 326 are connected to their neighbouring basal culturing chamber 323 by a microfluidic channel 324. Below each microfluidic channel 324 a normally open (NO) valve 348 is arranged.

The culturing module 301 mounted on the handling unit 302 is covered by a coverlid 303. For continuous perfusion additional features, to the ones mentioned above, are included but not limited to: access holes 327, vertical channels 328, a pierceable layer 329 and filters 330. The continuous perfusion, indicated by the black arrow and Q-dot, is created by applying positive and negative pressure, controlled by controllers, the access holes 327 in the handling unit 302 and the channels 328 in the culturing module 301, to the inlet well 325 and outlet well 326, respectively. Due to the pierceable layer 329 the pressure is contained in the system and a continuous flow can be generated. The filters 330 are used to avoid the entering of fluid, e.g., cell culture medium inside the channels 328. Therefore the filters 330 are permeable for one fluid such as air used for the actuation but impermeable for another fluid. To initially fill in the other fluid inside the culturing module 301, either the pierceable layer 329 is penetrated by e.g. a needle or the layer 330 is placed on the culturing module 301 after filling. The fluid in the outlet well 326 can be extracted similarly, either by penetrating the pierceable layer 329 or after removing the layers 329. Like this, the culturing module 901 can provide for an integrated continuous perfusion concept.

Figure 13:
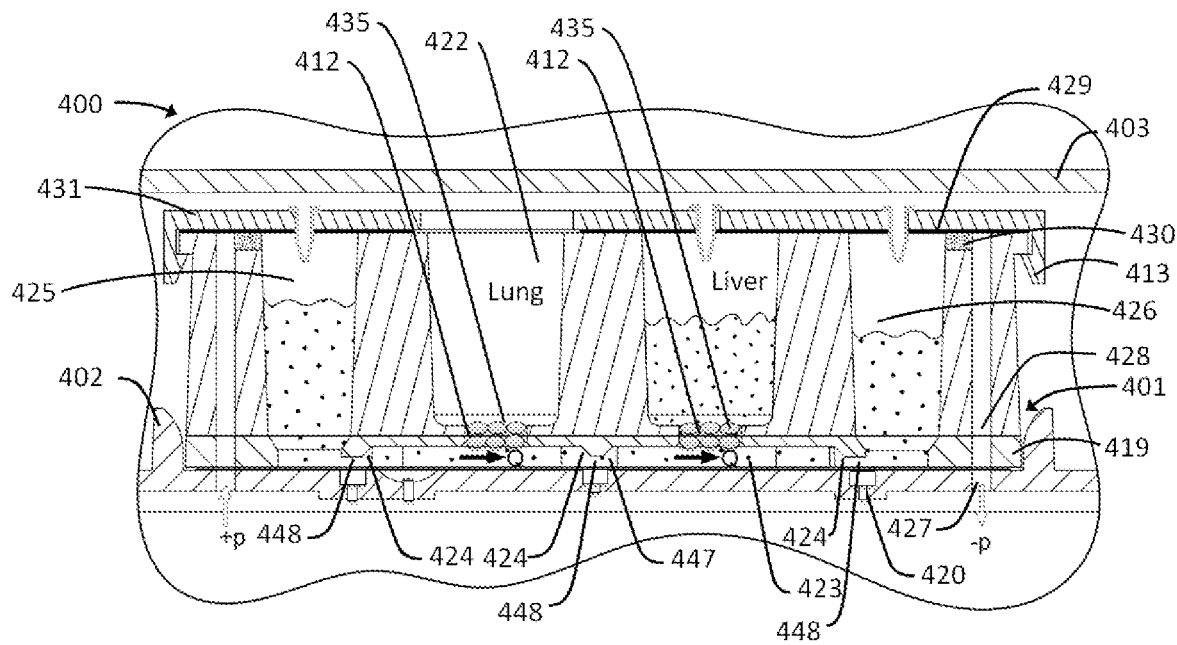
FIG. 13 illustrates a cross sectional view of a multi-organs system as a fifth embodiment of a cell culturing system according to the invention showing a lung-like tissue connected to a liver-like tissue.

FIG. 13 shows a fifth embodiment of a cell culturing system 400 according to the invention. The cell culturing system 400 comprises a culturing module 401 arranged on a handling unit 402. The culturing module 401 has two parallel rows of cell culturing wells each separated in an apical culturing chamber 422 and a basal culturing chamber 423 by a culturing membrane 412 which is sandwiched between an upper plate 418 and a lower plate 419 of the culturing module 401. The culturing module 401 further has series of inlet well 425 and outlet well 426. Each inlet well 425 is connected to the basal culturing chamber 423 of its neighbouring actuation chamber by a microchannel 424 which is connected to the basal culturing chamber 423 of its neighbouring actuation chamber by a microchannel 424 which is connected to the outlet well 426 by a microchannel 424. Between each two wells a normally open valve 448 is arranged.

The culturing module 401 mounted on the handling unit 402 is covered by a coverlid 403. Similarly as above, for continuous perfusion additional features are provided, i.e. access holes 427 in the handling unit 402, vertical channels 428 in the culturing module 401, pierceable layer 429, caps 931, hermetic access ports 936 and filters 430. The continuous perfusion, indicated by the black arrow and Q-dot, is created by applying positive and negative pressure to the inlet well 425 and outlet well 426, respectively. Due to the pierceable layer 429 the pressure is contained in the system and a continuous flow can be generated. The filters 430 are used to avoid the entering of fluid, e.g., cell culture medium inside the channels 428. The culturing module 401 is further closed by a cap 431 including the hermetic access ports 936 in the inlet well 425, the right actuation well and the outlet well 426. The apical culturing chamber 422 of the left actuation well is open. In the left open actuation well, e.g., lung cells 435 are grown and in the right closed actuation well, e.g., liver cells 435.

Also, a plurality of interconnected culturing wells can be added to mimic additional tissues in order for instance to reproduce the systemic response of specific compounds. A variety of organ-like tissues, such as the kidney, the liver, the brain, the gastro-intestinal tract, the skin, can be created with the cell culture system, either by seeding cells in suspension on the culturing membrane, or by adding formed spheroids, organoids or tissue slices in the culturing wells.

In use of the cell culturing system 400, the culture method can be the same as described earlier. Cells from a first cell type are first seeded in the first culturing well, and cells from a second cell type are then seeded in a second culturing well. Cells from different types can thus be cultured with different cell culture media until they are for instance fully differentiated. Once differentiated, the culturing module 401 is assembled to the handling unit 402.

Figure 14:
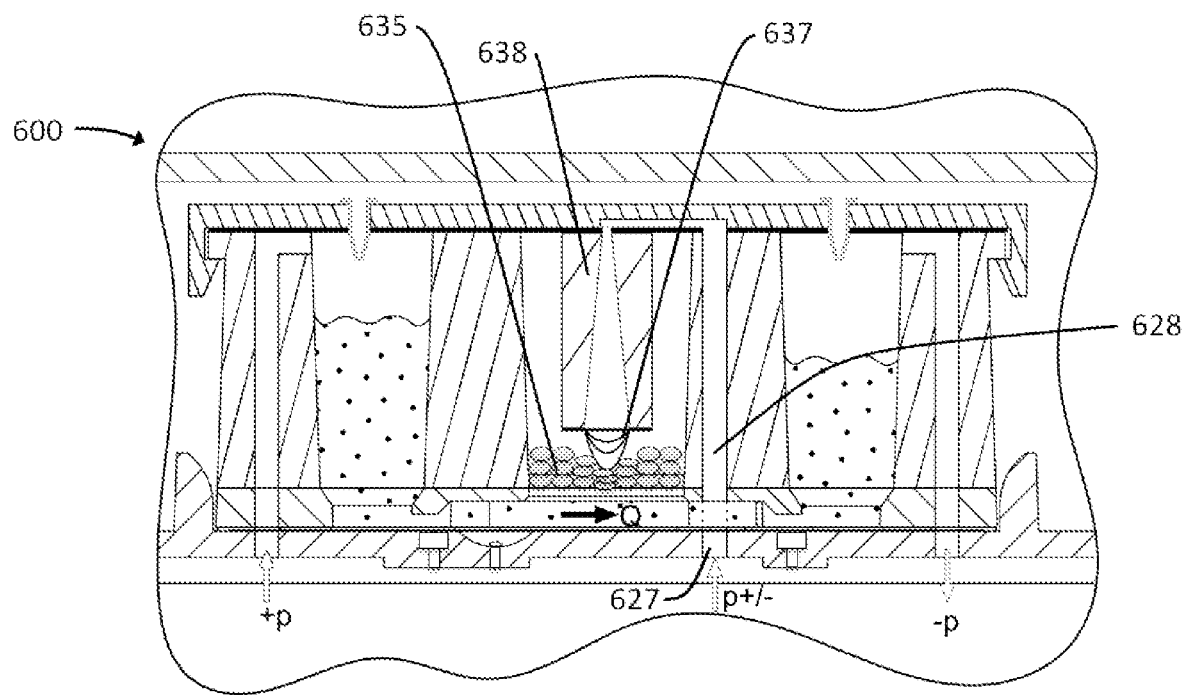
FIG. 14 illustrates a cross sectional view of a sixth embodiment of a cell culturing system according to the invention with tissue compressed by a membrane pressurized from a coverlid.

In FIG. 14 a sixth embodiment of a cell culturing system 600 according to the invention is shown. The cell culturing system 600 is very similarly embodied as the cell culturing system 900 described above. In contrast to this system the cell culturing system 600 comprises pressure posts 638 extending into the apical culturing chambers of the actuation wells. The pressure posts 638 have a hollow interior which at its top end passes over in a channel for pressurization 628 embodied in a culturing module. This channel passes over at its bottom into an access hole provided in a handling unit. The other end of the hollow interior of the pressure post 638 is covered by a compression membrane 637. By applying a positive pressure to the access hole, the compression membrane 637 deflects into the apical culturing chamber such that the pressure inside the latter is enhanced. Like this pressure inside the apical culturing chamber can be adjusted.

Figure 15:
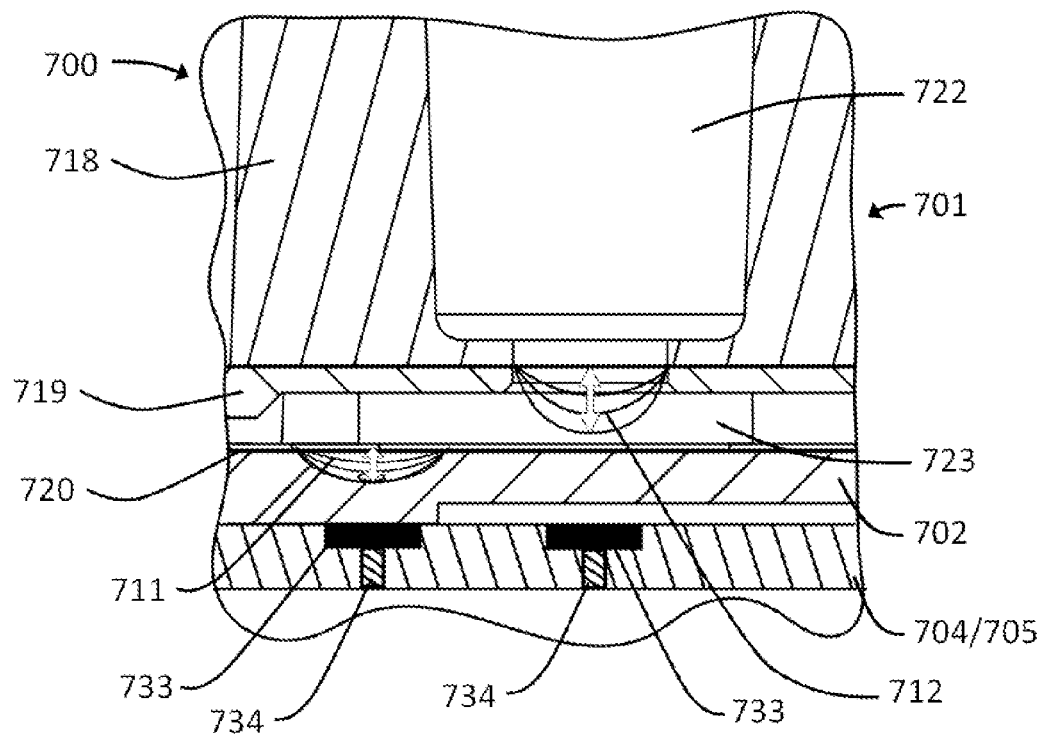
FIG. 15 illustrates a cross sectional view of a section of a culturing module of a seventh embodiment of a cell culturing system according to the invention that integrates sensors in a docking station.

FIG. 15 illustrates a seventh embodiment of a cell culturing system 700 according to the invention. The cell culturing system 700 comprises a culturing module 701 with an upper plate 718 and a lower plate 719. Between these two plates a culturing membrane 712 is arranged which separates a culturing well into a basal culturing chamber 723 and an apical culturing chamber 722. Between the culturing module 701 and the handling unit 702 an actuation layer 720 is sandwiched. The cell culturing system 700 further comprises docking stations 704/705 which are equipped with sensors 733 and sensor connectors 734. Here additional features, to the ones mentioned previously, are included but not limited to: the sensor 733 and the sensor connections 734. In this exemplary embodiment the sensors are integrated in the handling unit 702 and are used to monitor the deflection of the culturing membrane 712. The data is transferred from the sensor 733, via the sensor connection 734 to one or plural control units. There the data can be recorded and analysed and can, thus, be used to continuously monitor, control or change the specific action, here the deflection of the culturing membrane 712, over long time periods.

Figure 16:
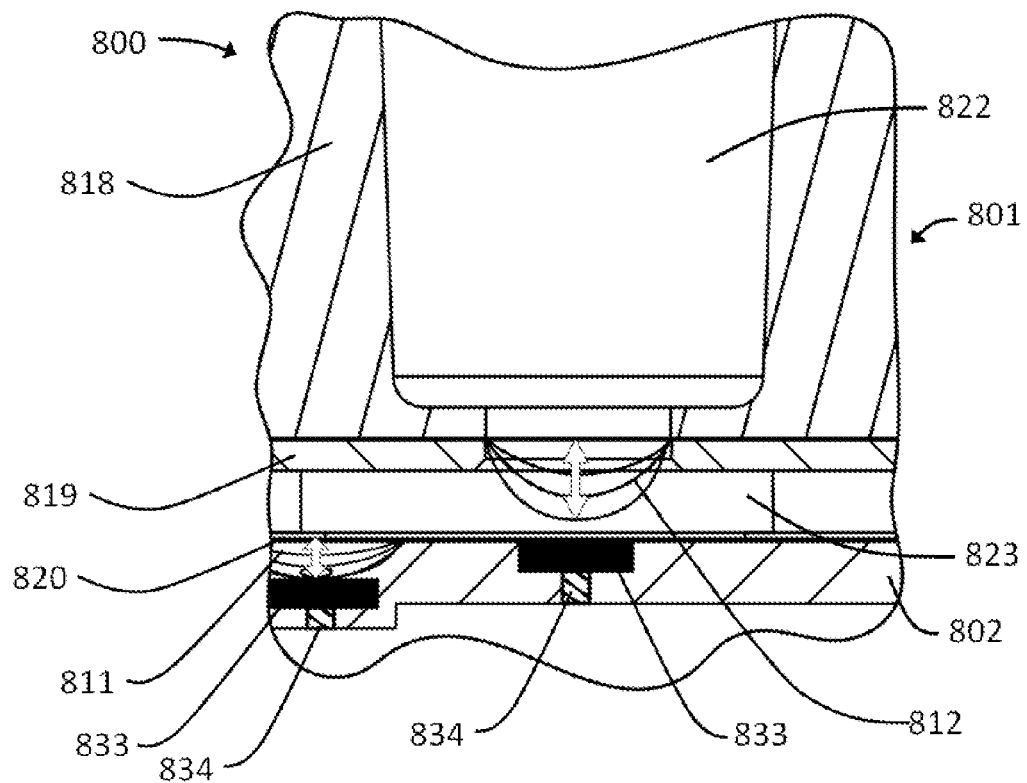
FIG. 16 illustrates a cross sectional view of a section of a culturing module of a eight embodiment of a cell culturing system according to the invention that integrates sensors in the handling unit.

In FIG. 16 a cell culturing system 800 is shown which is very similarly embodied as the cell culturing system 700 described above. The cell culturing system 800 comprises a culturing module 801 with an upper plate 818 and a lower plate 819, a culturing membrane 812 arranged between these plates which separates a culturing well into a basal culturing chamber 823 and an apical culturing chamber 822, and an actuation layer 820. In contrast to the above embodiment, the cell culturing system 800 further comprises sensors 833 and sensor connectors 834 which are provided in the handling unit 802.

Figure 17:
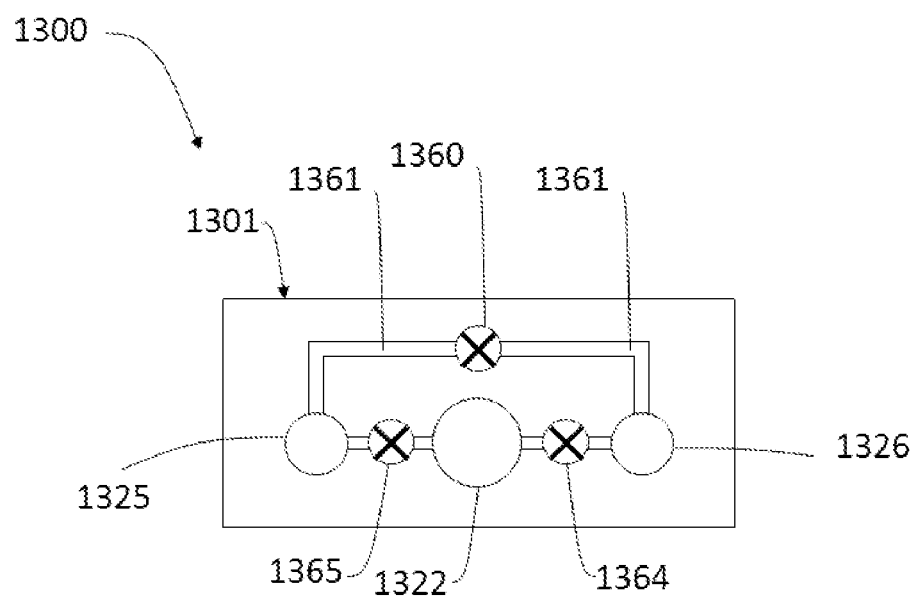
FIG. 17 illustrates the principle of a cell culture system with a recirculation flow between the outlet and the inlet wells.

FIG. 17 illustrates a ninth embodiment of the cell culture system 1300 according to the invention. The cell culturing system 1300 comprises a culturing module 1301, with a culturing well 1322, an inlet 1325 and an outlet 1326. Valves located between an actuation layer of a handling unit and of the culturing module 1364/1365 are on each side of a culturing well. Here an additional feature is the bypass channel 1361 that connects the outlet well to the inlet well. An additional valve 1360, also created between the actuation layer of the handling unit and the culturing module is located between the two wells.

This embodiment allows creating a recirculation flow. The cell culture medium perfused in the outlet well 1326 can be transported in the inlet well 1325. This allows for instance to increase the concentration of cytokines released by the cells to ease their detection, and most of all enables to better mimic paracrine, autocrine and endocrine signalling. Cellular waste products also recirculate and may be filtered by a kidney-like tissue.

Figure 18:
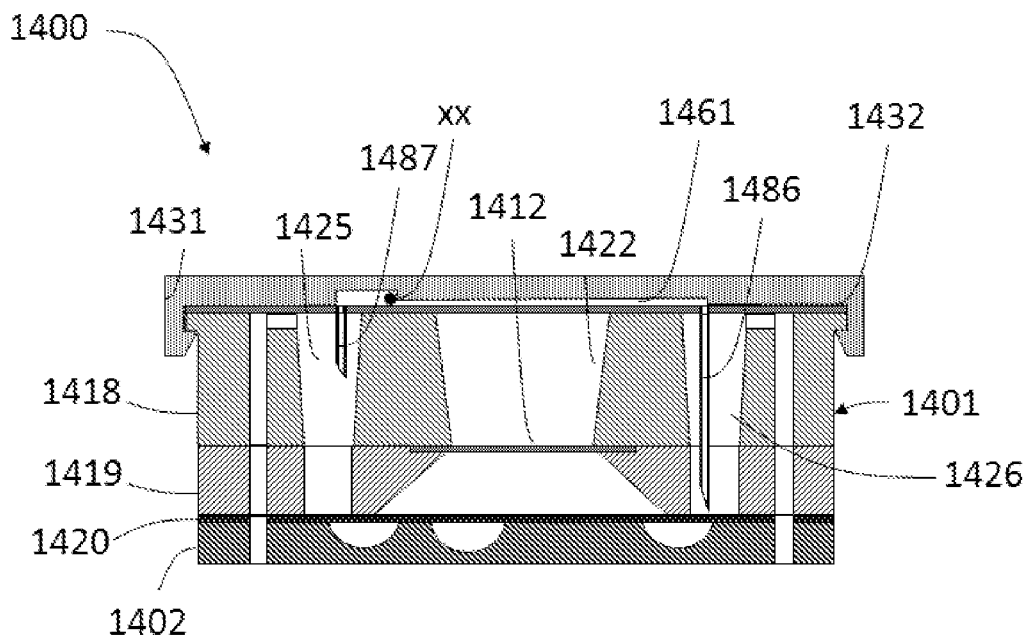
FIG. 18 illustrates a cell culture system with a cap air-tightly attached to a culturing module with two tubings or needles that plunge in the inlet and the outlet to transport the cell culture medium from the outlet to the inlet.

FIG. 18 illustrates a tenth embodiment of the cell culture system 1400 according to the invention. The cell culturing system 1400 comprises a culturing module 1401 seated in a docking station 1402, with a culturing well 1422, an inlet 1425 and an outlet 1426. The culturing module 1401 includes a lid 1431 with a sealing layer 1432. Here an additional feature is a bypass channel 1461 that connects the outlet well to the inlet well and is located in the lid 1431. Two needles/tubings 1486/1487 are directed towards the bottom of their respective outlet/inlet wells 1426/1425.

Figure 19:
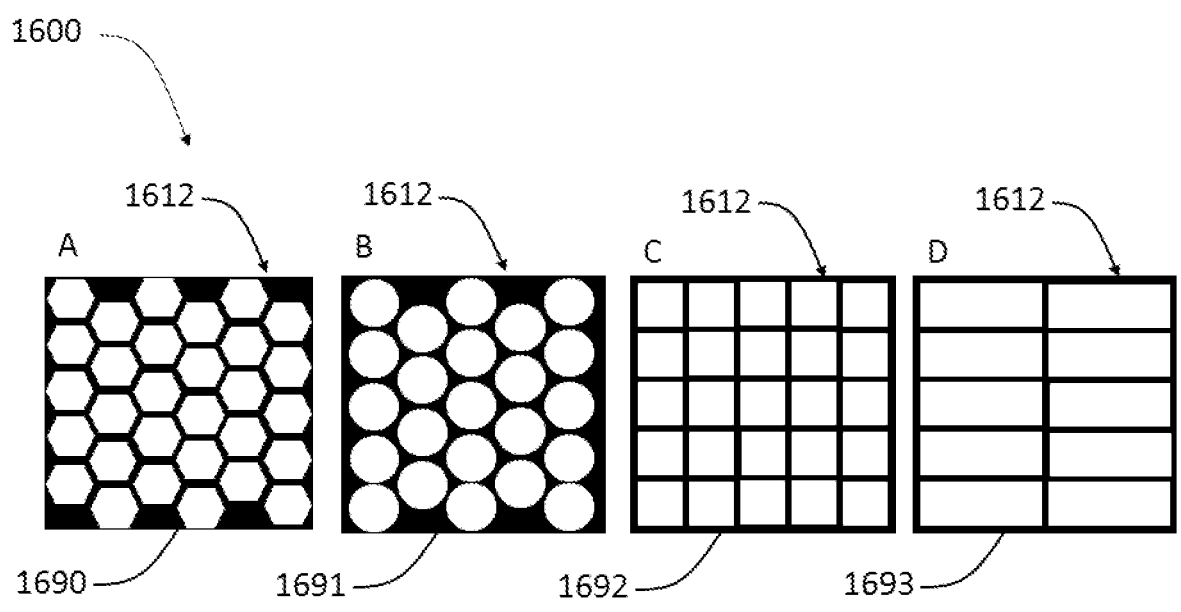
FIG. 19 illustrates various meshes that can be used to support the culturing membrane.

FIG. 19 illustrates a eleventh embodiment of the cell culture system 1600 according to the invention. The culturing membrane 1612 is made of a thin mesh 1690/1691/1692/1693 that serves as support and/or scaffold of the cell culturing membrane. The mesh is integrated in the culturing module between the top and the bottom plate, either by mechanical force, sandwiched between the two plates, by adhesion forces (glued, adhesive layer), or bonded to either the top of the bottom plate, by thermal bonding, or plasma bonding. The mesh can be made in metal (gold, titanium, tantalum, chromium, platinum, magnesium, iron, zinc, stainless steel, and alloys or any other materials typically used for stents) and produced by weaving, chemical etching, laser cutting, waterjet cutting, 3D printing, stamping, screen printing, plasma etching or the like. The mesh can also be made in hard or soft polymers, such as PS, COC, PMMA, PC, polyimide, PDMS, PU, and the like and produced by injection molding, hot embossing, stamping, laser cutting, waterjet cutting, chemical etching, plasma etching, 3D printing, spin coating and the like. Furthermore, the mesh can be made of cellulose or any other porous material that can be stretched. The mesh can also be made using techniques from the microelectronics/MEMS industries, using silicon, glass, polymers and other typical materials used for microfabrication. Silicon nitride, silicon dioxide, or the like, parylene meshes produced by thin film technologies, in particular photolithography, wet and/or dry etchings, can for instance be used as scaffold materials.

It is also envisaged that the mesh is made completely or partly of resorbable materials, such as pluronics, collagen, polylactic acid (PLA), poly-lactic-co-glycolide (PLGA) and the like. It can be produced by 3D printing, stamping, injection molding, dip coating, screen-printing or other similar techniques.

The mesh materials can also have different mechanical properties, such as stiffness and elasticity modulus, in order to create spatial gradients. Such arrangements can be used to induce cell migration, differentiation and maintenance and functional longevity. It is for instance envisaged that the mesh knots/intersections have a higher Young's modulus than the mesh lines.

In a specific culturing method, type I and type II alveolar epithelial cells are cultured on a mesh created with a mixture of collagen and elastin. Upon exposure to mechanical cyclic stress (physiological or pathophysiological), type I and type II alveolar cells will migrate towards the area with a larger stress, whereas type II cells would migrate towards the area with less stress, whereas type I cells may migrate in the area of a higher stress. A number of factors, such as the size of the alveoli, the amplitude of the mechanical stress, the type of cells seeded, the cell culture medium, the concentration of oxygen (a lower level of oxygen) and the air-liquid interface are key factors to induce the differentiation and maintain the functionality of alveolar cells.

The culturing membrane made of such a support/scaffold can be employed in engineering a variety of tissues including, but not limited to the cardiovascular system, lung, intestine, kidney, brain, bone marrow, bones, teeth, and skin. If the device is fabricated with a suitable biocompatible and/or biodegradable material, such as poly-lactic-co-glycolide acid (PLGA), it may be used for transplantation or implantation in-vivo. Moreover, the ability to spatially localize and control interactions of several cell types presents an opportunity to engineer hierarchically, and to create more physiologically correct tissue and organ analogs. The arrangement of multiple cell types in defined arrangement has beneficial effects on cell differentiation, maintenance and functional longevity.

In a specific embodiment, such scaffolds can be used to culture organ analogues, such as skin, lung, gastro-intestinal tract, urinary tract, and other tissues on larger surfaces, typically from several millimetres to several meters. Such scaffolds can be layered onto each other to create thicker tissues.

The mesh can further be used as support/scaffold for the culturing membrane is made of a conductive material, and can be used as an electrode to monitor the tissues or cellular constructs that is on or in proximity of the mesh. Changes of the cellular layer/barrier integrity can be detected that way using other electrodes located either in the apical or basal culturing chamber. The trans-epithelial electrical resistance can be monitored using such a configuration.

In a further embodiment, other three-dimensional scaffolds made for instance of electrospun fibers, or other porous materials, such as polysulfone, porous polyurethane, ceramic and the like, can be integrated in the cell culture system.

This description and the accompanying drawings that illustrate aspects and embodiments of the present invention should not be taken as limiting—the claims defining the protected invention. In other words, while the invention has been illustrated and described in detail in the drawings and foregoing description, such illustration and description are to be considered illustrative or exemplary and not restrictive. Various mechanical, compositional, structural, electrical, and operational changes may be made without departing from the spirit and scope of this description and the claims. In some instances, well-known circuits, structures and techniques have not been shown in detail in order not to obscure the invention. Thus, it will be understood that changes and modifications may be made by those of ordinary skill within the scope and spirit of the following claims. In particular, the present invention covers further embodiments with any combination of features from different embodiments described above and below.

The disclosure also covers all further features shown in the Figs. individually although they may not have been described in the afore or following description. Also, single alternatives of the embodiments described in the figures and the description and single alternatives of features thereof can be disclaimed from the subject matter of the invention or from disclosed subject matter. The disclosure comprises subject matter consisting of the features defined in the claims or the exemplary embodiments as well as subject matter comprising said features.

Furthermore, in the claims the word "comprising" does not exclude other elements or steps, and the indefinite article "a" or "an" does not exclude a plurality. A single unit or step may fulfil the functions of several features recited in the claims. The mere fact that certain measures are recited in mutually different dependent claims does not indicate that a combination of these measures cannot be used to advantage. The terms "essentially", "about", "approximately" and the like in connection with an attribute or a value particularly also define exactly the attribute or exactly the value, respectively. The term "about" in the context of a given numerate value or range refers to a value or range that is, e.g., within 20%, within 10%, within 5%, or within 2% of the given value or range. Components described as coupled or connected may be electrically or mechanically directly coupled, or they may be indirectly coupled via one or more intermediate components. Any reference signs in the claims should not be construed as limiting the scope.

What is claimed is:

1. A culturing membrane for mimicking in-vivo lung alveoli tissue comprising:
    a support with holes filled with extracellular matrix proteins, wherein the support is provided with a mesh, wherein the holes of the mesh have a dimension of about 200 µm to about 1000 µm in diameter, and wherein a thickness of the mesh is of about 1 µm to about 100 µm.

2. The culturing membrane of claim 1, wherein the extracellular matrix proteins are collagen, elastin, laminin, fibronectin or a combination thereof.

3. The culturing membrane of claim 1, wherein the pores of the support have a circular, quadratic, rectangular or triangular shape, or a combination thereof.

4. The culturing membrane of claim 1, wherein the mesh is made of polymer, metal, glass, silicon, silicon nitride, silicon oxide, a biodegradable material, cellulose, or a resorbable material.

5. The culturing membrane of claim 1, wherein a distance between the pores of the mesh are about 2 µm to about 200 µm.

6. The culturing membrane of claim 1, wherein a material of the mesh has differing mechanical properties to create spatial gradients.

7. The culturing membrane of claim 6, wherein the mechanical properties comprise stiffness and/or elasticity modulus.

8. The culturing membrane of claim 1, wherein the culturing membrane is elastic.

9. The culturing membrane of claim 1, wherein the culturing membrane is made of Polydimethylsiloxane, Polyurethane, Cyclic Olefin Copolymer, Polystyrene, Polycarbonate, Polypropylene and/or Poly (methyl methacrylate).

10. A method of producing a culturing membrane for mimicking in-vivo lung alveoli tissue made of components found in a basal membrane, comprising the steps of:
    using a mesh having holes, wherein the dimensions of the holes of the mesh are 200 µm to 1000 µm, and wherein a thickness of the mesh is of 1 µm to 100 µm; and
    providing a solution with the components found in the basal membrane on the mesh.

11. The method of claim 10, comprising a step of drying the culturing membrane.

12. The method of claim 11, comprising a step of hydrating the culturing membrane before use.

13. The method of claim 10, wherein the solution with the components found in the basal membrane is provided on the mesh by pipetting the solution on the mesh.

14. The method of claim 10, wherein the solution with the components found in the basal membrane is provided on the mesh by electro-spinning the solution.

15. The method of claim 10, wherein the components found in the basal membrane are collagen or elastin.

* * * * *